US011850353B2

(12) United States Patent
Dignum et al.

(10) Patent No.: US 11,850,353 B2
(45) Date of Patent: Dec. 26, 2023

(54) METHODS, INHALATION DEVICE, AND COMPUTER PROGRAM

(71) Applicant: VENTUS MEDICAL Limited, Liverpool (GB)

(72) Inventors: Mark Dignum, Liverpool (GB); David Lawson, Liverpool (GB)

(73) Assignee: Ventus Medical Limited, Liverpool (GB)

( * ) Notice: Subject to any disclaimer, the term of this patent is extended or adjusted under 35 U.S.C. 154(b) by 834 days.

(21) Appl. No.: 16/962,128

(22) PCT Filed: Jan. 10, 2019

(86) PCT No.: PCT/EP2019/050538
§ 371 (c)(1),
(2) Date: Jul. 14, 2020

(87) PCT Pub. No.: WO2019/141577
PCT Pub. Date: Jul. 25, 2019

(65) Prior Publication Data
US 2021/0052829 A1 Feb. 25, 2021

(30) Foreign Application Priority Data

Jan. 19, 2018 (GB) .................................... 1800875
Oct. 26, 2018 (GB) .................................... 1817440

(51) Int. Cl.
*A61M 11/04* (2006.01)
*A24F 40/53* (2020.01)
(Continued)

(52) U.S. Cl.
CPC .......... *A61M 11/042* (2014.02); *A24F 40/53* (2020.01); *A61M 15/06* (2013.01); *A24F 40/10* (2020.01);
(Continued)

(58) Field of Classification Search
CPC ............... A61M 11/042; A61M 15/06; A61M 2205/0211; A61M 2205/3368;
(Continued)

(56) References Cited

U.S. PATENT DOCUMENTS 6,845,216 B2  1/2005 Schuster et al.
10,506,829 B2 * 12/2019 Freelander ........ A61M 15/0023
(Continued)

FOREIGN PATENT DOCUMENTS

EP       2157873 B1      7/2011
GB       2543905 A       5/2017
WO    2016147188 A1      9/2016

OTHER PUBLICATIONS

European Patent Office, International Preliminary Examining Authority, International Preliminary Report on Patentability, Int'l App. No. PCT/EP2019/050538, dated Mar. 10, 2020.
(Continued)

*Primary Examiner* — Joshua Lee
(74) *Attorney, Agent, or Firm* — John H. Choi & Associates

(57) ABSTRACT

A method of controlling the generation of an aerosolised composition in an inhalation device having a heater arranged to heat an aerosolisable composition, the method comprising: controlling the power delivered to the heater such that the heater is heated from an ambient temperature to a first temperature, wherein the first temperature is below a temperature at which the aerosolisable composition is aerosolised; delivering a predetermined amount of power to the heater such that the temperature of the heater is increased from the first temperature to a second temperature, wherein the second temperature is greater than or equal to a temperature at which at least a portion of the aerosolisable composition is aerosolised.

20 Claims, 11 Drawing Sheets

(51) Int. Cl.
*A61M 15/06* (2006.01)
*A24F 40/10* (2020.01)

(52) U.S. Cl.
CPC ............... *A61M 2205/0211* (2013.01); *A61M 2205/3368* (2013.01); *A61M 2205/3653* (2013.01); *A61M 2205/52* (2013.01); *A61M 2205/8206* (2013.01)

(58) Field of Classification Search
CPC .. A61M 2205/3372; A61M 2205/3653; A61M 2205/50; A61M 2205/52; A61M 2205/8206; A24F 40/10; A24F 40/42; A24F 40/46; A24F 40/50; A24F 40/51; A24F 40/53; A24F 40/57; A24F 40/65; H02J 7/007192; H05B 1/02; H05B 3/20; H05B 3/748
See application file for complete search history.

(56) References Cited

U.S. PATENT DOCUMENTS

| | | | |
|---|---|---|---|
| 10,512,282 B2* | 12/2019 | Bowen | A24F 40/53 |
| 10,548,349 B2* | 2/2020 | Sur | A24F 40/50 |
| 10,588,176 B2* | 3/2020 | Marsh | A24F 40/46 |
| 10,638,768 B2* | 5/2020 | Flood | B01D 46/10 |
| 10,721,967 B2* | 7/2020 | Raichman | A24F 40/40 |
| 10,757,978 B2* | 9/2020 | Bessant | A24F 40/46 |
| 2015/0027459 A1 | 1/2015 | Collett et al. | |
| 2016/0271347 A1* | 9/2016 | Raichman | A61M 11/042 |
| 2017/0033568 A1 | 2/2017 | Holzherr | |
| 2018/0043114 A1* | 2/2018 | Bowen | A61M 15/003 |

OTHER PUBLICATIONS

European Patent Office, International Search Report, Int'l App. No. PCT/EP2019/050538, dated May 28, 2019.

* cited by examiner

METHODS, INHALATION DEVICE, AND COMPUTER PROGRAM

CROSS-REFERENCE TO RELATED APPLICATIONS

This application is a national stage application of International Application No. PCT/EP2019/050538 filed on Jan. 10, 2019, which claims priority to UK Application Nos. GB1800875.5 filed on Jan. 19, 2018 and GB1817440.9 filed on Oct. 26, 2018, which are incorporated by reference in their entireties.

FIELD

The present invention relates to a method of controlling the generation of an aerosolised composition in an inhalation device having a heater arranged to heat an aerosolisable composition. The present invention also relates to an inhalation device and a computer program operative in a programmable controller for an inhalation device for carrying out the method.

BACKGROUND

Pharmaceutical medicaments, physiologically active substances and flavourings for example may be delivered to the human body by inhalation through the mouth and/or nose. Such materials or substances may be delivered directly to the mucosa or mucous membrane lining the nasal and oral passages and/or the pulmonary system. One example of such a substance is nicotine which is consumed both for therapeutic or recreational purposes. Inhalation devices generally deliver the nicotine by vapourising or aerosolising the nicotine or a nicotine containing composition. Such devices may be powered or unpowered.

Vapourisation is the conversion of a substance into its gas phase at a temperature where the substance can also exist in the liquid or solid state, i.e. below the critical temperature of the substance. This can be achieved, for example, by increasing the substance's temperature or by reducing the pressure acting on it. Aerosolisation is the conversion of a substance into a suspension of tiny particles within a gas, i.e. an aerosol. Similarly, atomization is the process or act of separating or reducing a physical substance into fine particles and may include the generation of aerosols. Whilst the present application refers to the generation of an aerosolised composition, it will be appreciated that an aerosolised composition may also include a portion of the composition in its gaseous phase, i.e. a vapour. This is because a continuous state of equilibrium exists between a vapour and its condensed phases dependent on the atmospheric conditions.

In general, nicotine replacement therapies are aimed at people who wish to stop smoking and overcome their dependence on nicotine. There are currently a wide array of different nicotine replacement therapies already commercially available, but this present invention is concerned only with devices from which a vapour, aerosol, or similar airborne bolus, in most (but not necessarily all) cases containing nicotine, is inhaled by a user and whereby nicotine can be transferred to the bloodstream of a user. Nicotine delivery devices of this type are commonly further categorised as being "passive" or "active". An example a passive nicotine delivery device is an inhalator such as the Nicorette® Inhalator. This is an unpowered device (hence "passive") which allows a user to inhale a dose of nicotine but without the harmful combustion products of smoking a cigarette. The inhalator has the general appearance of a plastic cigarette and comprises a replaceable nicotine cartridge. When a user inhales through the device, nicotine vapours are released from the cartridge and are inhaled by the user. Nicotine replacement therapies are generally classified as medicinal products and are regulated by appropriate medicine regulations in the various countries in which they are sold, for example, the Human Medicines Regulations in the United Kingdom.

By contrast, active devices will commonly include a source of energy, such as electrical power from a battery, some means of excitation powered thereby, and a usually liquid solution containing nicotine which, when suitably excited, can be vaporised, atomised, aerosolised, or gasefied as the case may be to create an airborne nicotine-containing bolus which can be inhaled, usually through a mouthpiece provided at one end of the device. The vast majority of modern active devices are known as "electronic cigarettes" or "e-Cigs", and the solutions used in such devices will commonly comprise one or more of: propylene glycol (PG), polyethylene glycol (PEG), vegetable (VG) or some other glycerol, one or more flavourings, as well as nicotine itself. As with other nicotine replacement therapies, the underlying aim of such devices is to provide the user with a similar experience to smoking, both in terms of purely physical hand-to-mouth and vapour inhalation and exhalation aspects of smoking, and pharmacologically in terms of the delivery of the nicotine into the user's bloodstream.

In the vast majority of modern electronic cigarettes, the vaporization component will consist of a simple resistive heater in the form of one or more wire coils or planar heating elements which is disposed in contact with or in close proximity to an amount of the solution to be aerosolised, and both heater and the solution are commonly provided within a larger component which additionally acts as a reservoir for the solution. Such components are commonly known by the portmanteau "cartomizer", being a combination of the words "cartridge" and "atomizer". Finally, as their name suggests, electronic cigarettes commonly include electronic control circuitry operable to actuate the heater responsive to an actuation signal, such from a dedicated switch provided in some suitable position on the device or possibly from some other sensing means, such as an air-flow or pressure change sensor whereby the device can detect when a user is drawing air through the mouthpiece by inhaling.

The skilled reader should understand that the term "electronic cigarette" (or "e-Cig", "e-Cigarette") as used herein includes, without limitation, electronic nicotine delivery systems (ENDS), electronic cigarettes, e-cigarettes, e-cigs, vaping cigarettes, pipes, cigars, cigarillos, vaporizers and devices of a similar nature that function to produce an aerosol mist or vapour that is inhaled by a user. Some electronic cigarettes are disposable; others are reusable, with replaceable and refillable parts.

FIG. 1 shows a known vaporisation component 1 for a conventional e-cigarette. The vaporisation component comprises a wick 3, which may be solid or flexible, with a heating coil 5 wrapped around it. Hence, the component is generally termed a wick-and-coil heater. In the e-cigarette, the wick is in fluid communication with a cartridge (not shown) containing an e-liquid and is saturated with the e-liquid. The heating coil 5 is connected to a power source 7 by means of a switch 9 for activating the heating coil. The switch 9 may be a button actuatable by user or a flow switch for detecting a user's inhalation through the e-cigarette.

The wick 3 generally contains more e-liquid than would be vaporised during a single inhalation. This increases the thermal mass of the wick 3 and means that the heat generated by the coil 5 is unnecessarily expended in heating all of the e-liquid rather than the amount that actually needs to be vaporised. Heating surplus liquid reduces the energy efficiency of the device. Furthermore, the coil 5 is spaced apart from the wick 3 to prevent the coil 5 from burning the wick 3. This reduces heat transfer to the wick and means that the coil 5 has to be powered to a higher temperature than that necessary to merely vaporise the e-liquid, i.e. typically around 300° C., in order to compensate for the dissipation of heat and inefficiencies of heating a large substrate and volume of liquid.

Upon activation by switch 9, an electric current is passed through the coil 5 thereby heating the coil. This heat is transferred to the e-liquid in the wick 3 causing it to vaporise. FIG. 2 shows a graph of temperature T (y-axis) versus time t (x-axis) and a typical heating profile of heating coil 5. The heating coil 5 is activated at time $t_1$ results in a rapid increase in temperature from the ambient temperature $T_{amb}$ to an operating temperature $T_\theta$ which is greater than or equal to a vaporisation temperature of the e-liquid. The change in temperature is denoted by $\Delta T$. Release of switch 9 at time $t_2$ causes the temperature to return to $T_{amb}$. Each time switch 9 is operated, an amount of electrical power is delivered to heating coil 5 which is determined by the current through the coil and the voltage across it. This results in a change in temperature $\Delta T$. In warmer climates with higher ambient temperatures this can result in higher operating temperatures than would be achieved in colder climates. If operating temperatures are too high, excess e-liquid may be vaporised and/or undesirable by-products generated resulting in a poor quality aerosolised composition. These can result in the user receiving a higher than intended dose or an unpleasant sensation for the user such as throat irritation or an unpleasant taste. In particularly extreme cases, high operating temperatures may generate by-products which are potentially harmful. On the other hand, if ambient temperatures are very low then the heating coil 5 may not generate sufficient heat to vaporise the e-liquid which can also be undesirable.

FIG. 3 shows a comparison of two separate heating profiles A1 and A2 of a heating coil starting at different ambient temperatures, $T_{amb1}$ and $T_{amb2}$. In heating profile A1, the change in temperature $\Delta T$ caused by activation of the heating coil 5 results in an operating temperature below a maximum temperature $T_{max}$, i.e. a temperature at which undesirable by-products are generated. However, the ambient temperature $T_{amb2}$ in heating profile A2 is higher than that in A1 and the resulting temperature change $\Delta T$ causes the operating temperature to rise above $T_{max}$, potentially vaporising too much e-liquid or creating unwanted by-products. Indeed, one of the pervasive problems with conventional e-cigarettes is their consistency of operation, in particular as regards both achieving and maintaining a consistent operating temperature $T_\theta$, and as regards creating a consistent airborne bolus (in terms of volume and constituent composition) for inhalation with each and every successive activation of the device. One important contributing factor to both these particular issues is the ambient air temperature, $T_{amb}$, where the device is being or is about to be used. Another factor, at least for basic "fixed voltage" devices, is that there is little if any precise electronic control of the heating element, for example in terms of the voltage applied across it or the power delivered to it.

More recent devices are addressing these latter issues, and there do now exist so-called "variable voltage" (VV), "variable wattage" (VW), and temperature control (TC) devices which either directly measure or indirectly calculate the current operating characteristics of the heating element, in particular its actual real-time temperature and/or its electrical resistance. Such devices afford users the following flexibilities:

VV: a user selects a desired operative voltage level, being usually less than the maximum rated voltage of the battery, typically 2.5-5V; in use, the electronic control circuits appropriately modulates or otherwise actively controls the voltage applied across the heating element so that it remains essentially uniform throughout activation, thus promoting consistency of operation; VV operation does not take any account of the (usually varying) resistance of the heating element, but for some heater coil materials (e.g. some Nichrome & Kanthal® alloy varieties) the temperature coefficient of resistance is so low ($<<10^{-3}$ K$^{-1}$) as to be negligible, so simple VV operation can achieve much more consistent vapour production than basic direct connection of the battery to the heating element;

VW: a user selects a desired power delivery value; commonly employed 3.5-5V batteries can deliver power a range typically between 1-250 W, depending largely on the resistance of the heating element; as the skilled reader will understand, by virtue of Ohm's law, selecting a specific desired wattage automatically takes account of the resistance (R) (power being equal to $V^2/R$), and therefore even if the resistance of the heating element varies significantly during activation as its temperature rises from ambient to somewhere in the range 150 deg. C.-300 deg. C., power delivered is electronically controlled to remain constant; VW operation thus facilitates significant flexibility in operation, and allows for a wide array of different heater elements to be used, as well as ensuring consistency of operation;

TC: more recent devices permit some degree of temperature control (or temperature protection) in that the user selects a specific desired (and/or maximum) element operating temperature; once selected, the electronics within the device (see, e.g., digitally programmable electronic controllers from Evolv LLC, and electronic cigarettes employing TC from ELeaf under the brand-name "iStick Pico") ensures that the heating element operates at a desired temperature and/or does not overheat, i.e. rise above the desired maximum temperature;

In order for TC to be achievable in relatively simple digitally programmable electronics devices, it is necessary for the heating coil to be made of a material with a substantial non-negligible temperature coefficient of resistance (TCR or "α"), because the temperature of the heating coil is not measured directly, but calculated from the dynamically measured coil resistance; calculation of temperature is then achieved using the linear approximation $$R(T)=R(T_{amb})(1+\alpha\Delta T),$$

where R (T) is the resistance at Temperature T,
R ($T_0$) is the resistance at some ambient Temperature $T_{amb}$,
α is the temperature coefficient of resistance (presumed constant over the operating temperature range, and known in advance for various common materials), and
$\Delta T = T_{ACTUAL} - T_{amb}$, i.e. the difference between the current temperature and the ambient.

It is worth mentioning that most TC devices will also provide some element of VW control, because it is now commonly believed that it is the power delivered to the heating coil which is the primary determining factor in the efficacy of vapourisation/aerosolisation for any given primarily PG/PEG-based liquid formulation. In short, the higher the delivered wattage, the more extensive the vaporisation/aerosolisation will be, resulting in the generation of larger smoke plume volumes for the user to inhale (and subsequently exhale). However, although increased power delivery may result in the creation of large vapour plumes, VW devices are still rather primitive and their existence has come about more from a desire on the part of users for larger and more visible smoke plumes, as opposed from any desire to deliver a plume which is consistent as regards its composition of PG/PEG and (most importantly) nicotine.

Thus, despite the above advances in electronic control, problems of inconsistent device operation still remain, particularly in regions of the world where ambient air temperatures can vary significantly or are extreme in that the average ambient temperatures are significantly greater or less than that in more temperate regions. Naturally, specifically customizing individual devices according to territories in which they will be used is impractical for manufacturers. Furthermore, while VV/VW/TC devices might afford some improvements in terms of aerosol consistency, it is still unlikely that any essentially wick-and-coil type e-cigarette device, whether fixed voltage, VV, VW or TC, will ever achieve a nicotine dosing consistency which is essentially uniform across multiple successive inhalations, and therefore, analogously, it is unlikely that such devices would or could ever receive the requisite regulatory approval to enable them to be medically prescribed by doctors, and to be labelled and marketed through medical and healthcare channels as nicotine replacement therapies. Indeed any device which is capable of being refilled with an arbitrary, user-sourced liquid (as any conventional wick-and-coil device with a reservoir certainly is) is most unlikely to receive regulatory approval as there is, by definition, little or no control over the quantity of the controlled substance, i.e. nicotine, which may be present in the liquid formulation or in any aerosol produced therefrom.

In response to such safety and quality concerns, a number of countries have introduced or are proposing to introduce stricter rules governing the marketing of tobacco products. For example, the European Union has agreed a revised Tobacco Products Directive (Tobacco and Related Products Regulations 2016) which stipulates specific requirements relating to the safety and quality of tobacco products, in particular nicotine-containing liquids for use in e-cigarettes.

Aspects and embodiments of the invention were devised with the foregoing in mind.

SUMMARY OF THE INVENTION

In a first aspect, the present invention provides a method of controlling the generation of an aerosolised composition in an inhalation device as prescribed in claim 1 hereof.

This first aspect of the present invention has many advantages over conventional devices, even those which claim to offer some pre-heating functionality. Firstly, the skilled reader will understand that the present invention can ensure that heaters within devices can now accurately and repeatably be pre-heated to the correct temperature "from cold", i.e. when the device has not been operated for some time and its temperature, and more importantly the temperature of the heater element within it, will be substantially the same as the ambient air temperature.

To expand further, it will be appreciated that merely setting pre-heat power (wattage) and time constraints (as is possible on some more advanced devices) is insufficient because applying a set amount of power for a set amount of time will always cause the temperature of heating element to rise by a correspondingly set amount. If ambient temperature is already elevated, it is possible that the so-called pre-heat function could actually elevate the heating element temperature above the aerosolisation temperature, which is of course unacceptable and possibly dangerous if little or no aerosolisable composition remains. Conversely, if current ambient temperature is significantly reduced, for example in habitually cold climates, delivering a set amount of power for a set amount of time will only result in unsatisfactory warming of the heating element, resulting in slower activations, and possibly incomplete and/or highly variable aerosolisations. The present invention overcomes these problems by determining the ambient temperature substantially in advance of a first pre-heating step and then using the value determined to adjust the power delivered to the heating element during at least this heating step so that the heater is reproducibly heated to the same second temperature regardless of the ambient temperature, every time the device is initially switched on. Once the heater element has been raised to the correct (known) pre-heat temperature, this ensures that each subsequent heating and cooling steps (ie. from the first temperature to the aerosolisation temperature and back again), are similarly standardised, and very accurately controllable. By such means it is therefore possible to accurately and precisely control the aerosolisation such that a reproducible quantity and quality of aerosolised composition is delivered each time the heater is heated to the second (aerosolisation) temperature. Of course, in providing such precision and flexibility of control, the present invention also allows for progressively changing quantities and possibly also qualities of the aerosols created, should this be desired. Furthermore, the increased accuracy of power control mean that the second temperature is always maintained well below a temperature at which excess aerosolised composition or harmful by-products are produced.

The first temperature can be termed a preconditioning temperature, i.e. an intermediate, sub-aerosolisation temperature to which the heater is heated prior to heating to a temperature at which aerosolisation occurs. A further advantage of heating to a first temperature which is below the aerosolisation temperature is that controlled, steady heating to such a temperature may assist in conditioning or homogenising the aerosolisable composition prior to heating to the second temperature. For example, if constituent ingredients of the aerosolisable composition have separated during storage, heating the heater to the first temperature (and thus in turn heating the aerosolisable composition) may help to remix the ingredients and improve the consistency and quality of the aerosolisable composition. This advantage applies equally to the second aspect of the invention further described below and which specifically requires that the first rate of heating and the second rate of heating are different, the latter being preferably much quicker than the former. Naturally, a relatively slow and steady first heating rate, which occurs over a typically longer period than that during which aerosolisation is to occur (e.g 5 s-1 m or more for the pre-heating, as opposed to 1-5 s or less for aerosoliation), can further promote homogeneity and consistency of the composition if any separation of the constituents therein has occurred, or if it is particularly viscous as a result of being cold. Also, pre-heating naturally results in a more speedy generation of the aerosolised composition when the device is activated which results in a more satisfying experience for the user.

The preconditioning described above provides a yet further advantage, particularly where the heater itself is mounted on or otherwise directly supported by a substrate, such as a metal, ceramic, glass or plastics material substrate. In prior art devices, particularly in wick-and-coil devices, the phenomenon of hot spots can occur frequently, wherein some very small portion of the coil and or the wick (1 mm or less) becomes disproportionately hot (>300-400 deg. C.) compared to the remainder. When this occurs, the aerosolisable composition in the vicinity of the hot spot is immediately not only vapourised, but partially or substantially pyrolised, leading to unpleasant and potentially harmful chemicals being present in the aerosol. By contrast, where both the heater and the substrate on which it is disposed are preconditioned, preferably at a desired rate of heating, heat is transferred to the substrate itself so that its temperature is also raised, and provided the rate of heating is not too rapid and sufficient time is allowed for heat to flow within the substrate body, the substrate is also accordingly preconditioned and furthermore in a manner such that its temperature is substantially uniform throughout, and the same as that of the heater. In this manner, the issue of hot spot generation can be largely eliminated. Also, it is believed that preconditioning the substrate in this manner further promotes consistency in the subsequent aerosolisations which will occur thereon and immediately above said substrate. Yet further, such preconditioning largely precludes thermal shocks from arising in both substrate and heater.

In preferred embodiments, maintaining the heater at any one or more of the first temperature, the second temperature and the third or subsequent temperatures is achieved by dynamically measuring the heater temperature or a value representative thereof and comparing with one or more previously stored corresponding values, and controlling the power to the heater accordingly.

The step of controlling the power delivered to the heater in order that the heater reaches and is maintained at different desired temperatures may be achieved in a variety of different ways. In one embodiment, a value representative of the heater temperature may be compared to the desired temperature in order to determine an error between the measured temperature and the desired temperature, and a correction may subsequently be applied, dependent on the error value, to reduce said error over time by regulating the power provided to the heater to drive the measured temperature towards the desired temperature. A feedback mechanism, such as a proportional-integral-derivative (PID) control loop may be used to control the power delivered. Various sensors, for example, a thermistor, may be used for measuring the temperature, or the heater temperature may be estimated based on a real-time measurement of its resistance.

The first temperature may be in the range of 25° C. to 90° C., more particularly in the range of 30° C. to 70° C., and yet more particularly in the range of 35° C. to 50° C. The second temperature may be in the range 120° C. to 180° C., more particularly in the range 130° C. to 160° C. The skilled person will appreciate that the second temperature, and therefore the amount of power that needs to be delivered, may be selected based on the choice of aerosolisable composition and its constituent ingredients and the temperature at which these vaporise.

Device activation, i.e. typically short periods of time (<1-5 s or less) when aerosolisation is desired, may be achieved in different ways, for example by use of a simple switch, or possibly automatically by using an inhalation or other suitable air pressure sensor.

In preferred arrangements, the initially determined ambient temperature (or a value representing it) may be stored, for example in memory means provided within the device. Further preferably, the stored ambient temperature may retained in such memory while the device remains operative (i.e. effectively switched on). In some embodiments the memory storage may be volatile so that when the device is placed into an inoperative state (i.e. it is switched off, either purposefully by a user or automatically by control electronics determining that a predetermined period of time has elapsed without any activations having occurred), any previously stored ambient temperature value is simply wiped from such memory. In other embodiments, the memory may be more permanent, and either a previously measured ambient temperature value may be overwritten when the device is next switched on, or some form of running record may be maintained of all previously measured ambient temperature values. In some preferred embodiments, use of look-up tables, pre-stored in non-volatile memory, for correlating measured heater resistance values with temperature is contemplated.

Most preferably, ambient temperature-dependent control of power to heater is effected during one or both of: when the heater is being heated from the initial ambient temperature to the first temperature, and when the heater is cooling from the second temperature to the third temperature. Furthermore, in some preferred embodiments, ambient temperature-dependent control of power may be performed such that the first heating rate is significantly slower than the second heating rate. It should also be noted that although cooling rate will inevitably be dependent, at least to some extent, on the ambient temperature, it may be desirable to lessen or in some way modify the natural rate of cooling to prolong the life of the heater. As will be understood by the skilled reader, rapid and repeated heating and cooling (between the first, second and third temperatures) may progressively weaken and degrade the heater, and heater performance may be compromised as a result, so controlling the power to the heater when cooling such that it cools more slowly or according to some predetermined cooling profile can be advantageous. It is also worth mentioning here that the theoretical maximum or natural cooling rate of the heater is largely determined according to Newton's law of cooling, which in its simplest form states that the rate of heat loss of a body is dependent on the difference in the temperatures between the body and its surroundings. It is therefore immediately apparent not only that the ambient temperature is equally important during cooling as it is during heating, at least from the ambient temperature to the first temperature.

Optionally, the heater may be heated such that it returns to the third or subsequent temperature after being heated to the second temperature less than 25-50 times, and more particularly less than 20 times, and yet more particularly between 8 and 15 times. A typical cigarette provides an average of around 15 inhalations but, depending on the inhalation strength of a particular user, may be between 10 and 20 inhalations. Cigars typically provide an average of 25 inhalations but over a longer period than a cigarette.

For the avoidance of doubt, Applicant considers that the feature of differential first and second heating rates is an entirely and completely separately claimable aspect of the present invention, and in this regard, the present invention further provides a method of controlling the generation of an aerosolised composition in an inhalation device having an electrically resistive heater arranged to heat an aerosolisable composition, the method comprising:

upon an initial operation of the device, controlling the power supplied to the heater such that the heater is heated at a first heating rate from an ambient temperature to a first temperature and thereafter maintaining the heater at said first temperature, said first temperature being below an aerosolisation temperature of the aerosolisable composition;

while the device is operative and upon a first or subsequent activation thereof, controlling the power supplied to the heater such that the temperature of the heater is increased at a second or subsequent heating rate from the first temperature to a second temperature and thereafter maintaining the heater at said second temperature, said second temperature being greater than or equal to the aerosolisation temperature, after one of: the first or any subsequent activation is completed, the elapsing of a predetermined period of time since the first or a subsequent activation, and receiving a first or subsequent deactivation request, controlling the power supplied to the heater such that the temperature of the heater decreases at a first or subsequent cooling rate from the second temperature to a third or subsequent temperature and thereafter maintaining the heater at said third or subsequent temperature, said third or subsequent temperature being below the aerosolisation temperature but above the ambient temperature, characterised in that, the power to the heater is specifically controlled in a manner which ensures one or more of: the first heating rate is slower than the second heating rate, and the first or any subsequent cooling rate is modified as compared to the natural cooling rate which would occur if no power whatsoever was delivered to the heater during a notional time from any deactivation of the heater until it reached the third or subsequent temperature.

By "slower" in the above is meant that an average of the first heating rate (measured in K/s and taken over the time that heating is occurring) is less than the corresponding average second heating rate. Preferably the first heating rate is between 1-8 times slower than the second heating rate.

It should be mentioned that preferred features and embodiments of the first aspect of the present invention should be considered as being equally applicable to, and separately claimable with reference to, the second aspect of the present invention, and vice versa.

The present invention, in aspects relating either to the specific temperatures to which the heater is cyclically heated or to aspects concerned with the heating and/or cooling rates, is particularly applicable to devices which utilise a cartridge containing a predetermined amount of aerosolisable composition, and which is specifically designed to be substantially entirely aerosolised after a fixed number of inhalations, e.g. after 5-20 (usually) consecutive activations of the device. Such devices are quite different from the conventional wick-and-coil devices because such conventional devices commonly include a reservoir containing a relatively much larger supply of liquid aersolisable composition which perpetually soaks the wick, and which may last, depending on device usage frequency, for many days before the reservoir containing the liquid requires refilling. By contrast, cartridge-type devices, to which the present invention is particularly applicable, commonly comprise a substrate on which a fixed amount of a carefully formulated aerosolisable composition is provided, and which is intended to be completely or mostly aerosolised over a discrete period of time equivalent to that commonly taken by users of conventional tobacco products to obtain their fix of nicotine therefrom. For example, a habitual cigarette smoker will smoke a number of cigarettes every day, and each cigarette may entail 4-10 separate discreet inhalations. Cartridge-type devices may be designed such that they mimic the consumption of a single cigarette, that is each individual cartridge is provided with a sufficient amount of aerosolisable composition accurately dosed with nicotine at the required concentration such that both the following occur:

After any single device usage session, comprising for example 4-20 discrete device activations (i.e. inhalations), substantially all the aerosolisable composition is aerosolised, and the cartridge is effectively spent and must be replaced anew before the next device usage, and The amount of nicotine delivered to the user during any single session is approximately equivalent to (or slightly less or more, depending on individual user preference or requirements) the amount of nicotine which would generally be delivered by a conventional tobacco product in approximately the same time, e.g. the amount of formulation provided on any single cartridge, and the nicotine concentration therein, may be carefully adjusted to provide a broadly identical pharmacological effect, in terms of nicotine delivery to taking, for example, 6 inhalations on a single cigarette over a 6 minute period. (Obviously there are infinite variations on this general theme, as the skilled reader will understand, and this example is provided only to illustrate the principle).

One reason that the present invention is particularly applicable to cartridge-type devices, and one which may not be immediately obvious to the skilled reader, is that, with each and every device activation (i.e. one single inhalation), not only does the amount of composition significantly change, but the nicotine concentration in the remaining composition may also change. Furthermore, depending on the particular formulation, the chemical and physical characteristics of the composition may also change appreciably between each device activation. Given the change in both the volumetric amount of aerosolisable composition and (potientially) the variation in the concentrations of the chemical constituents thereof between each and every successive activation, any one of the following functionalities or any combination thereof may be desirable, especially as regards ensuring a consistent or progressively increasing or decreasing concentration of nicotine in successive aerosols produced by the device during any single activation:

Controlling the power delivered to the heater differently during each successive device activation such that the second temperature (i.e. at which the composition is aerosolised) is progressively changed, for example progressively and/or gradually increased or lowered, either between successive device activations or during any single activation, to take account of the diminishing amount of composition remaining both after successive activations, and during any single individual activation;

Controlling the power delivered to the heater different during each of the first and/or any successive cooling of the heater such that either or both of the cooling rates and the third or subsequent temperatures is progressively changed between successive device activations; for example the third temperature and subsequent temperatures may be progressively increased so lowered, and first and successive cooling rates may be similarly altered so as to be progressively faster or slower between successive activations;

Controlling the power to the heater such that any of the first, second and third or subsequent temperatures at which the heater is maintained is progressively changed during any time when the heater temperature is desired to be so maintained.

These functionalities should be considered as being separately claimable features of the present invention, in whatever aspect it may be expressed. However, much simpler embodiments of the invention are of course also possible, for example in which:

The third and subsequent temperatures are the same as the first temperature, and remain essentially constant, The first or any subsequent cooling rates are identical, and possibly also controlled such that they are broadly, on average, identical in magnitude to the second heating rate, The second temperature (at which aerosolisation is to occur) is maintained constant between any two successive device activations, and does not vary during any single activation, The time for which the device can remain activated remains fixed, constant and unvarying between any two successive activations.

The skilled reader will immediately understand that a cartridge-type device with one or more of these specific functionalities can be adapted to precisely deliver a desired amount of nicotine in each successive aerosol, and indeed such a device can now provide a heretofore unprecedented degree of nicotine dosage control. When it is considered that, for medical nicotine replacement therapies, the dosing regime of nicotine is vitally important, the skilled person can immediately understand the benefits and advantages of the present invention.

A yet further preferred feature of the present invention, and one which provides yet further enhanced flexibility, is the facility for the device to determine a representative value for the length of time of the first and/or each and every successive activation, store this value, and subsequently control the power to the heater during any further subsequent activation in dependence on this value so determined. This feature is particularly advantageous, because the device can now make its own assessment of the amount of composition remaining in the cartridge currently in use, provided of course that the device is programmed in advance with certain cartridge-specific information. Such information may be quite varied and extensive and might include:

some indication as to the volumetric amount of aerosolisable composition provided on a new cartridge of that type, the chemical constituent formulation of the composition, in particular regarding at least the nicotine concentration, and the concentrations of the usual precursor substances such as PG, PEG and VG, as well as other contaminants such as flavourings and the like.

In some preferred embodiments, there is provided a further step of monitoring an amount of time having elapsed since any previous activation, and if this monitored amount of time exceeds a previously stored threshold value (for example 2-5 m), then the device is automatically returned to an inoperative state, ie. It is automatically switched off.

In a third aspect, the present invention provides an inhalation device configured to carry out the method described above. In particular, the present invention provides an inhalation device configured to generate an aerosolised composition for inhalation by a user, the device comprising: a heater arranged to heat an aerosolisable composition; and a controller to control the power delivered to the heater; wherein the controller is configured to control the power delivered to the heater as prescribed in the methods above.

The inhalation device may further comprise components which interface with or are otherwise in communication with the controller, for example:

at least one electrically resistive heater element, which may, for example, be screen-printed on a substrate; using a conductive ink or conductive printable paste; examples include carbon-based ink, a conductive ink comprising any one or more of silver, ruthenium and palladium, or other conductive elemental or alloy material having a relatively high temperature coefficient of resistance; the substrate may comprise a material selected from one or more of a ceramic, a plastics and glass;

a sensor, for example some form of switch to detect a user operating the device, that is, switching it on, a second sensor, such as an air flow or pressure drop sensor, which can provide an indication that a user is inhaling through the device, and whereby first and subsequent activations of the device can be initiated, and possibly also thereafter the deactivation of the device can be automatic, i.e. when inhalation ceases;

a PID or other suitable feedback controller.

Where the heater is provided on a, preferably substantially planar, substrate an amount of the aerosolisable composition is preferably provided on and supported on the substrate. Accordingly, the substrate, the (screen-printed) resistive heater element and aerosolisable composition may form a cartridge-like replaceable consumable which can be received within an inhalation device and replaced once the aerosolisable composition has been expended.

The heater may comprise a first resistive heater element configured to heat to the first temperature and a second resistive heater element configured to heat to the second temperature. This allows the first and second resistive heater element to be controlled independently.

In a fourth aspect, the disclosure provides a computer program operative in a programmable controller for an inhalation device to implement the methods described above. Implementing the control of the device in software as opposed to hardware reduces the part count of the device and may allow the size of the device to be reduced.

Viewed from a fifth aspect, the disclosure provides a computer readable storage medium having stored thereon a computer program described above.

BRIEF DESCRIPTION OF THE DRAWINGS

One or more specific embodiments in accordance with aspects of the present invention will be described, by way of example only, and with reference to the following drawings in which:

FIG. 1 is a schematic diagram of a prior art e-cigarette wick-and-coil heater.

FIG. 2 is a graph of temperature versus time showing a heating profile of a typical wick-and-coil heater.

FIG. 3 shows a comparison of two separate heating profiles of a typical wick-and-coil heater starting from different ambient temperatures.

FIG. 4 shows a comparison of two heating profiles according to an embodiment of the present invention starting from different ambient temperatures.

FIG. 5 shows a heating profile according to an embodiment of the present invention in which the heater is heated to a second temperature a plurality of times, and clearly illustrating the different heating rates between ambient temperature and pre-heat temperature, and then subsequently between the pre-heat temperature and an aerosolisation temperature, FIGS. 5A-5E shows various different heating profile possible and according to various different aspects and embodiments of the present invention, as explained further below, FIG. 6 is a schematic illustration of an inhalation device according to an embodiment of the present invention.

DETAILED DESCRIPTION OF THE INVENTION

Figure 1:
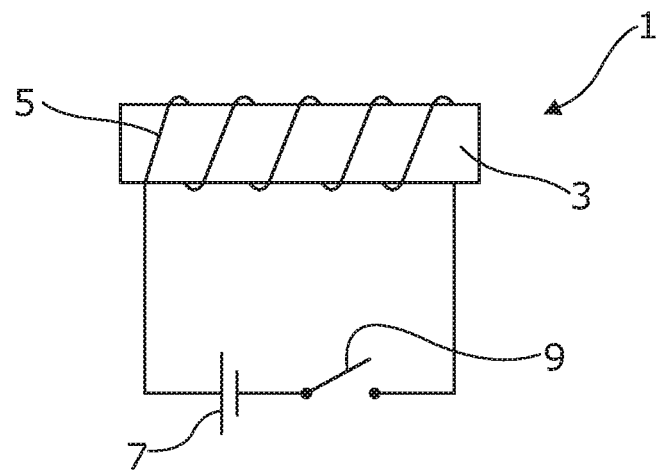
Figure 2:
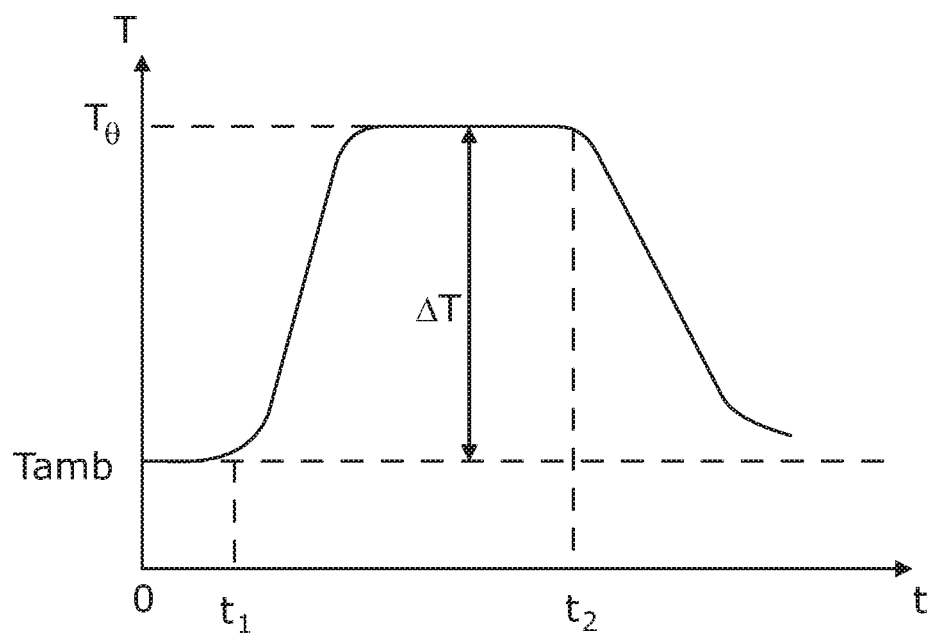
Figure 3:
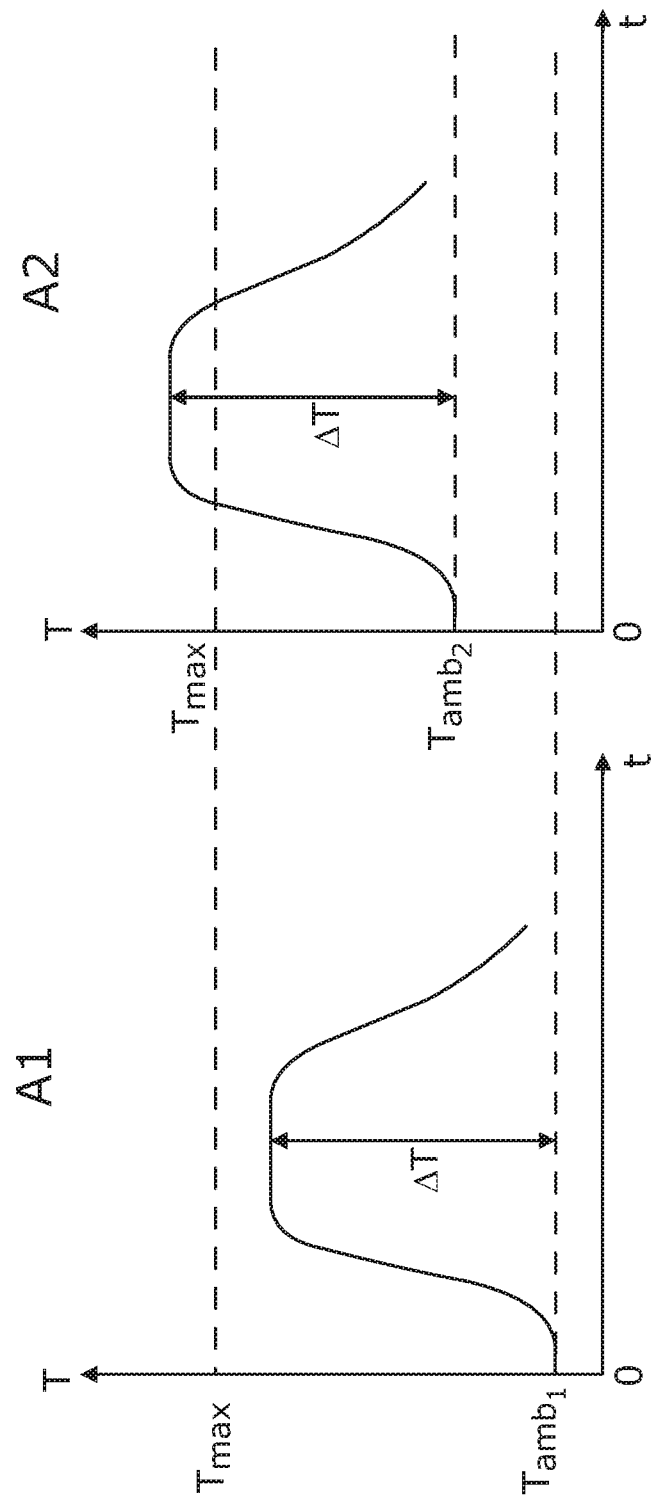
Figure 4:
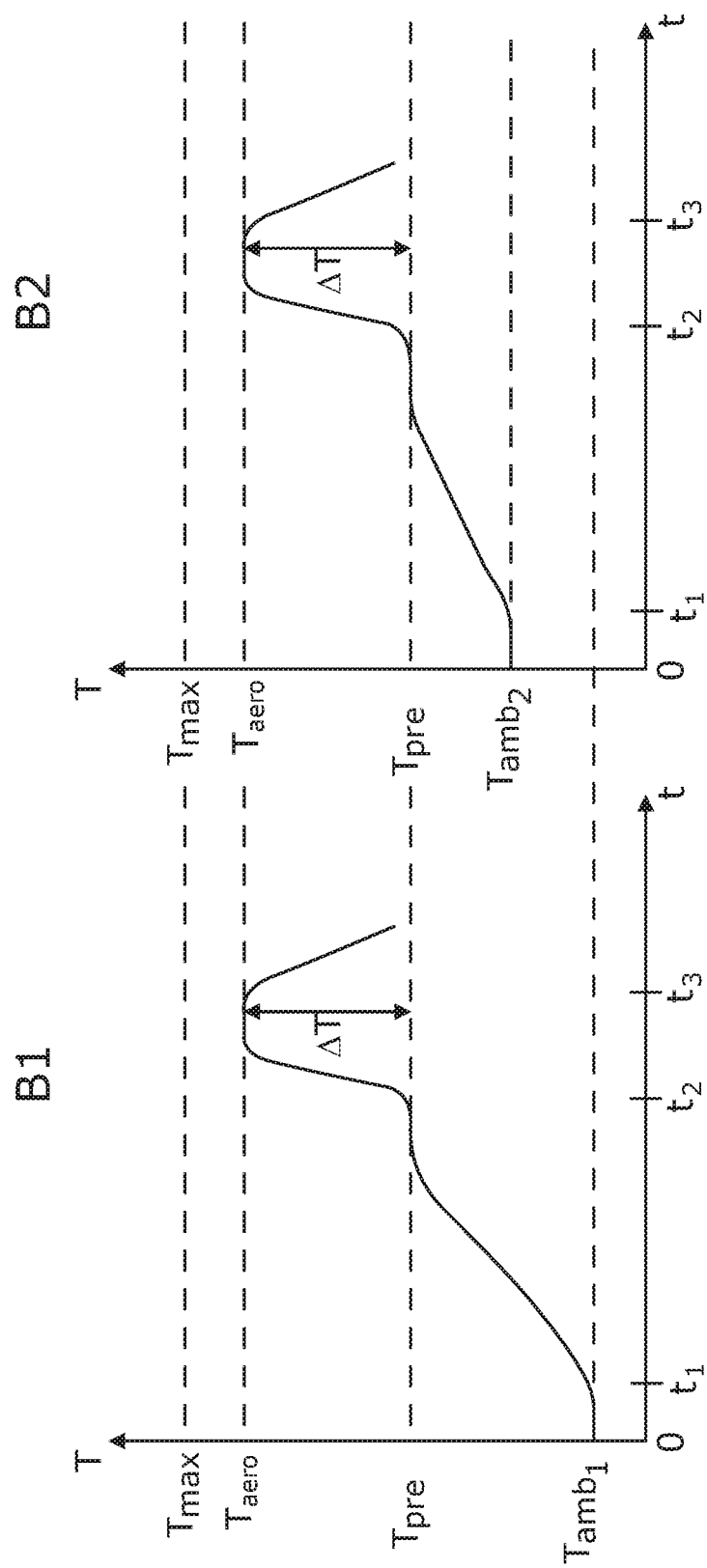

FIG. 4 shows a comparison of two separate heating profiles B1 and B2 for a heater of an inhalation device, which profiles are produced by a method according to the present invention. The heater is arranged to heat an aerosolisable composition. Each heating profile starts from a different ambient temperature $T_{amb1}$ and $T_{amb2}$ and are not drawn to scale.

In both heating profiles B1 and B2, a heater is initially heated to a first temperature or preconditioning temperature $T_{pre}$. The preconditioning temperature $T_{pre}$ is the same in both heating profiles regardless of the starting ambient temperatures and may typically be in the range 5° C. to 45° C. higher than the ambient temperature, depending of course on ambient temperature norms for the particle climate, country or region in which the device is to be used. The preconditioning temperature $T_{pre}$ is preferably one of the ranges 25° C. to 90° C., 35° C. to 80° C., 45° C. to 70° C.

The heater starts heating, notably relatively gradually, towards the preconditioning temperature $T_{pre}$ in response to the device being caused to enter an initially operative state by a user at time $t_1$, for example, by pressing a switch to activate the device. In short, the user switches the device on. At this time, or very shortly thereafter, the device makes some determination of the ambient temperature and stores this determined value for later use. In both heating profiles B1 and B2, the power delivered to the heater is controlled so that the temperature of the heater increases with time towards the preconditioning temperature $T_{pre}$, and such control is dependent on the determined value for ambient temperature. It will generally take less than one minute for the heater to reach the preconditioning temperature $T_{pre}$. However, this can be reduced to 30 seconds or less if required. That is to say, the power delivered to the heater by the device controller can be modified so that a desired rate of heating can be achieved. Both the rate of heating and the preconditioning temperature $T_{pre}$ itself may depend at least in part on the particular choice of aerosolisable composition used. Different compositions may benefit from different initial heating rates and different preconditioning temperatures.

Once the temperature has stabilised at the preconditioning temperature $T_{pre}$, and in some embodiments, not before, a user can activate the device for a second time, for example, by pressing the same switch again, possibly in a different manner (e.g. a double-click type operation, or a press-and-hold type operation), or by pressing an alternate switch, or (if the device is provided with pressure drop and/or air flow sensors), inhaling through the device. This is shown at time $t_2$ in both heating profiles B1 and B2. An indicator such as an illuminated light emitting diode (LED) may notify a user that the heater has reached the preconditioning temperature $T_{pre}$ and is therefore ready to be activated into an aerosolisation mode. In response to such activation, a predetermined amount of power is delivered to the heater to increase the temperature to a second temperature or aerosolisation temperature $T_{aero}$, which is greater than or equal to a temperature at which at least a portion of the aerosolisable composition is aerosolised. This generates an aerosolised composition which can be inhaled by a user through the device. The aerosolisation temperature $T_{aero}$ is below a maximum temperature $T_{max}$ at which excessive aerosolisation occurs or at which undesirable by-products are generated. Note in particular the significantly faster rate of heating (in both profiles) after activation at time $t_2$.

The temperature of the heater is ideally maintained at the aerosolisation temperature $T_{aero}$ for the duration of a single activation (while an inhalation occurs), which is generally between two and three seconds in length. Aerosolised composition is therefore generated for the duration of the inhalation. In both heating profiles B1 and B2, at time $t_3$, the user's inhalation comes to an end, and either as a result of inhalation ceasing, or if the user releases an activation switch on the device, the power provided to the heater is significantly reduced such that the temperature relatively rapidly decreases. In some embodiments, the power supplied to the heater during this cooling is a trickle-type or in the form of a periodic low pulse so that its temperature can continue to be estimated. Of course, in the case a thermistor, thermocouple or other temperature detection device is used adjacently or in contact with the heater element, and on a different circuit from that to which power is supplied to the heater, then of course it is not necessary to directly supply any power to the heater, but there are simplicities of construction (i.e. Dedicated temperature measuring components are not required) if trickle- or pulse-type low power is supplied to the heater as it cools. Once the temperature of the heater has been determined as having returned to the preconditioning temperature $T_{PRE}$, then power is again increased to the heater so that it is subsequently maintained at that temperature pending the next activation. If a second activation of the device is not forthcoming within a predetermined amount of time, for example, two to five minutes, the device will automatically enter an inoperative state, i.e. it shuts itself down and ceases providing power to the heater to save energy and prevent the aerosolisable composition being degraded. After the device shuts down in this manner, or if forcibly shut down by the user, the device and the heater within it will naturally return to ambient temperature. How quickly this occurs depends on the temperature differential between the device and heater temperatures upon shut down and the ambient temperature, but under normal circumstances this might be expected to occur over a period of 5 m-60 m.

As briefly mentioned above, the heater is heated to the aerosolisation temperature $T_{aero}$ at a significantly faster rate than the rate at which the heater is heated to the preconditioning temperature $T_{pre}$. This assists in the rapid generation of the aerosolised composition such that it can be inhaled earlier in the user's inhalation producing a more satisfying experience for the user. It also increases the chances of the aerosolised composition reaching deeper into the user's lungs and reduces the chances of it being exhaled.

Heating to the preconditioning temperature $T_{pre}$ at a slower rate also provides more time for preconditioning or homogenising the aerosolisable composition and reduces the likelihood of heating the aerosolisable composition too quickly from an ambient temperature which may result in a poor quality aerosolised composition being generated, for example, due to the generation of undesirable by-products or certain constituents of the aerosolisable composition being generated in preference to others due to separation during storage.

A temperature change $\Delta T$ from the preconditioning temperature $T_{pre}$ to the aerosolisation temperature $T_{aero}$ results from the delivery of a predetermined amount of power to the heater. Since the heater is heated to the preconditioning temperature $T_{pre}$ before a user activates the device to generate an aerosolised composition for inhalation, the change in temperature $\Delta T$ resulting from the delivery of the predetermined amount of power to the heater reproducibly results in the same aerosolisation temperature $T_{aero}$ being achieved. This produces a standardised and repeatable amount and quality of aerosolised composition for inhalation. In other words, the user experiences the same inhalation experience regardless of the ambient temperature.

Figure 5:
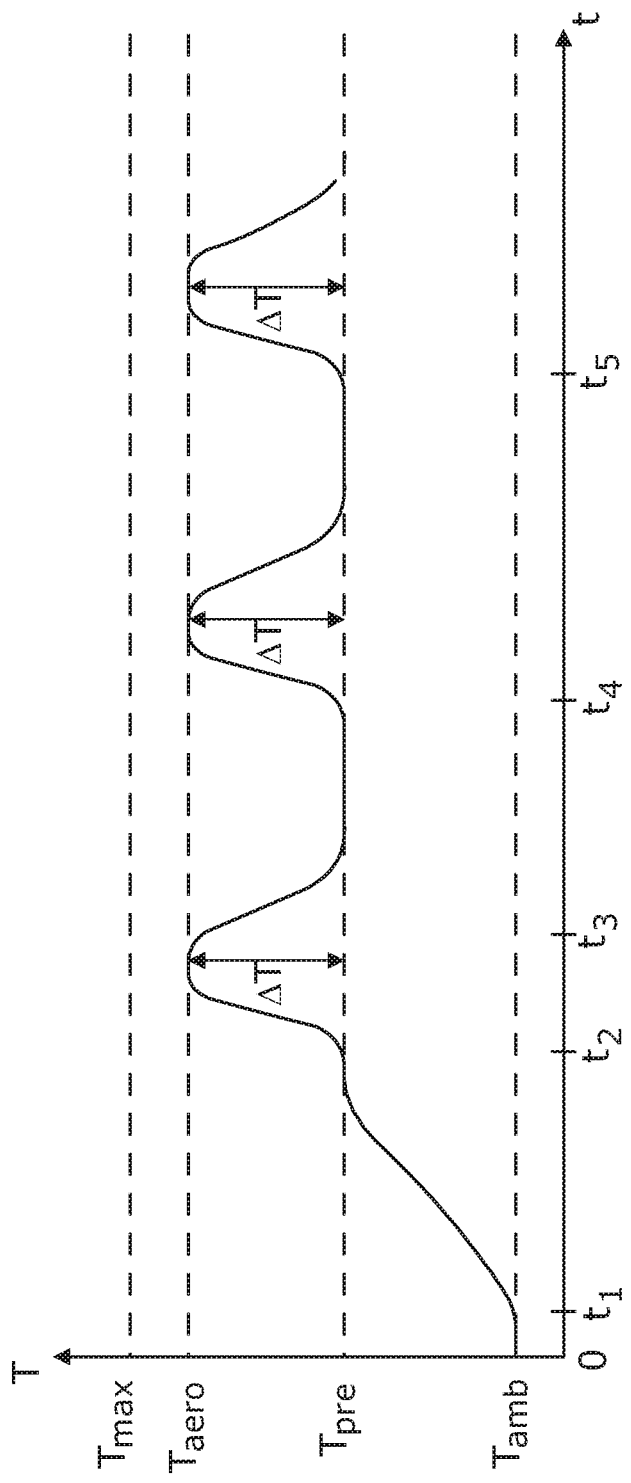

Turning now FIG. 5, a heating profile is shown for a heater of an inhalation device in which the heater is heated to a second temperature or aerosolisation temperature $T_{aero}$ a plurality of times. Up to time $t_3$, i.e. the time when a user finishes their first inhalation, the heating profile is identical to the profile shown in heating profile B1 of FIG. 4. However, in FIG. 5, the power delivered to the heater is controlled such that the temperature returns to the first temperature or preconditioning temperature and awaits a further subsequent activation by the user. Therefore, the aerosolisable composition relatively quickly cools to and then remains at the preconditioning temperature $T_{pre}$ in its conditioned and homogenised state ready for the subsequent activations of the device, which occur at times $t_4$ and $t_5$ respectively. In between the activations occurring at times $t_4$ and $t_5$, the power delivered to the heater is controlled such that the temperature again returns to the preconditioning temperature rather than returning to the ambient temperature. This produces a standardised and repeatable amount and quality of aerosolised composition for each inhalation such that the user experiences the same inhalation experience each time regardless of the ambient temperature. It can also be seen in FIG. 5 that the temperature differential between $T_{aero}$ and $T_p$re, $\Delta T$, remains essentially constant. There can be advantages to both maintaining $\Delta T$ constant for each successive device activation, and also to varying $\Delta T$, for example increasing or reducing it, or translating it (i.e. where $\Delta T$ is the same, but between adjusted values of $T_{aero}$ and $T_{pre}$) between successive device activations, as will be further explained below with reference to FIGS. 5A-5E.

Figure 5A:
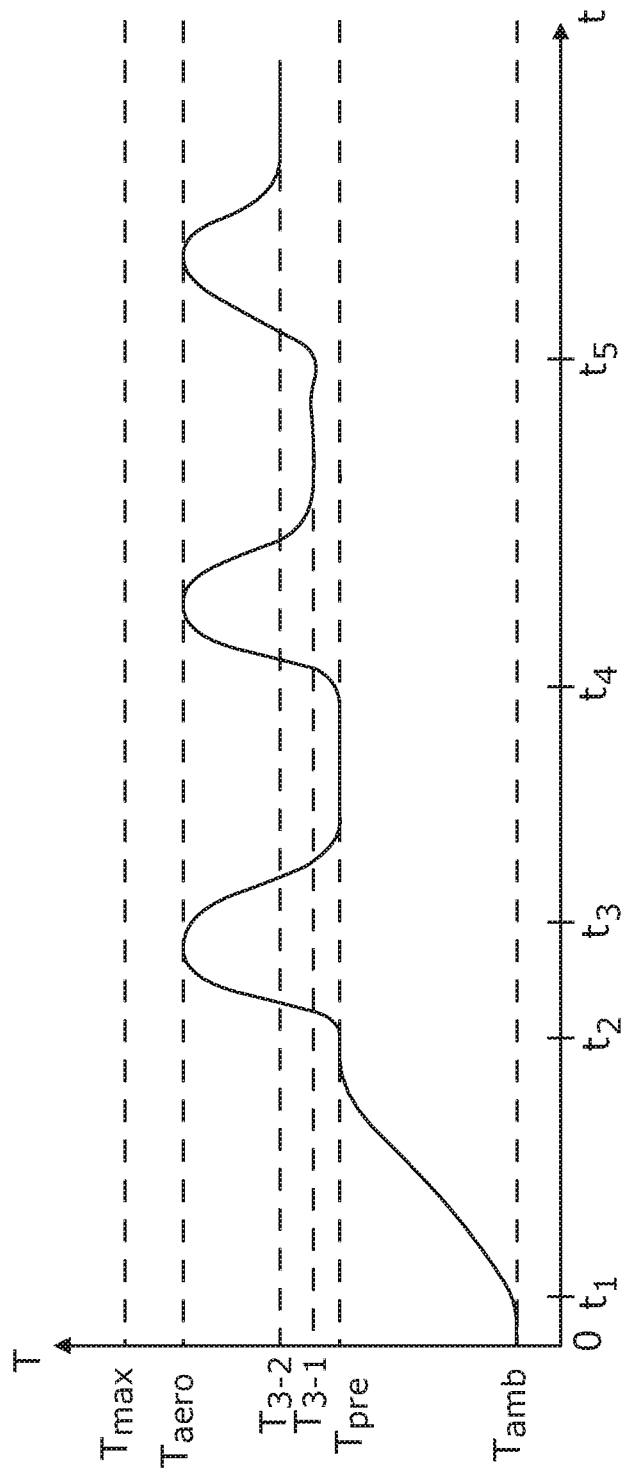
Figure 5B:
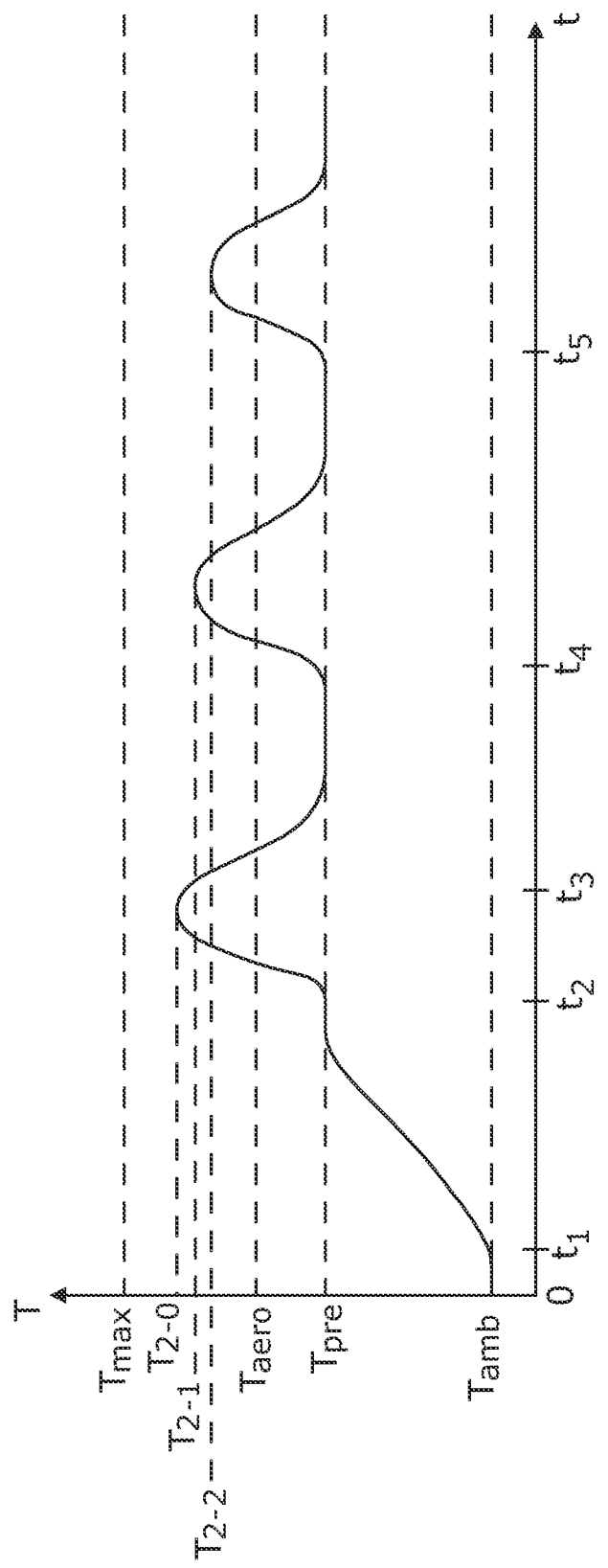

Referring now to FIG. 5A, which shows a slightly modified profile as compared to FIG. 5, it can be seen from this Figure that although the first activation at time $t_2$ is essentially the same as that in FIG. 5, the next activation at time $t_1$ is modified in that the heater is only allowed to cool to a slightly elevated preconditioning temperature $T_{3-1}$. Furthermore, for the third activation starting at time $t_5$, the heater element is only allowed to cool to a yet further slightly adjusted preconditioning temperature $T_{3-2}$. Thus, by carefully controlling the power to the heater as it cools, the preconditioning temperature can be progressively changed—in FIG. 5A it is progressively increased between successive activations, but of course it could equally be progressively decreased if desired, ort indeed follow some prescribed pattern, if desired. In FIG. 5B, it can be seen that, instead of controlling the power to the heater during the cooling stage to modify the resulting preconditioning temperature at which it is desired to maintain the heater prior to a subsequent activation, it is equally possible to control the power to the heater during the heating from any preconditioning temperature $T_{pre}$ to a progressively adjusted aerosolisation temperature. As can be seen in the Figure, the initial aerosolisation temperature is $T_{2-0}$, and this temperature is progressively reduced for subsequent aerosolisations, to $T_{2-1}$ for the activation occurring at time $t_4$, and to $T_{2-2}$ for the activation occurring at $t_5$. Again, although in this Figure a progressive reduction in the aerosolisation temperature as between successive aerosolisations is illustrated, any progressive, random, uniform or non-uniform change can be implemented if desired. Note in this Figure that the temperatures $T_{2-0}$, $T_{2-1}$, $T_{2-2}$ are shown as being above the aerosolisation temperature $T_{aero}$, which in this embodiment is to be understood as being the minimum temperature at or above which aerosolisation can occur.

This provides the device of the present invention with incredible flexibility as far as delivering a prescribed dosing regime is concerned, whether for nicotine or indeed any other drug or composition which can be administered to a patient as part of an inhalable vapour. For aerosolisable compositions for which it becomes increasingly difficult promote the active constituent into the aerosol, progressively higher aerosolisation temperatures may be used, and conversely for aerosolisable compositions for which it becomes increasingly easy promote the active constituent into the aerosol, progressively lower aerosolisation temperatures may be used. In each case, the ultimate result will be that the concentration of the active constituent in the aerosol produced will be essentially identical over multiple successive aerosolisations. Of course, other dosing regimes may be preferable, and the skilled reader will immediately appreciate the ease and simplicity with which the present invention may be adapted to provide any dosing regime desired.

Figure 5C:
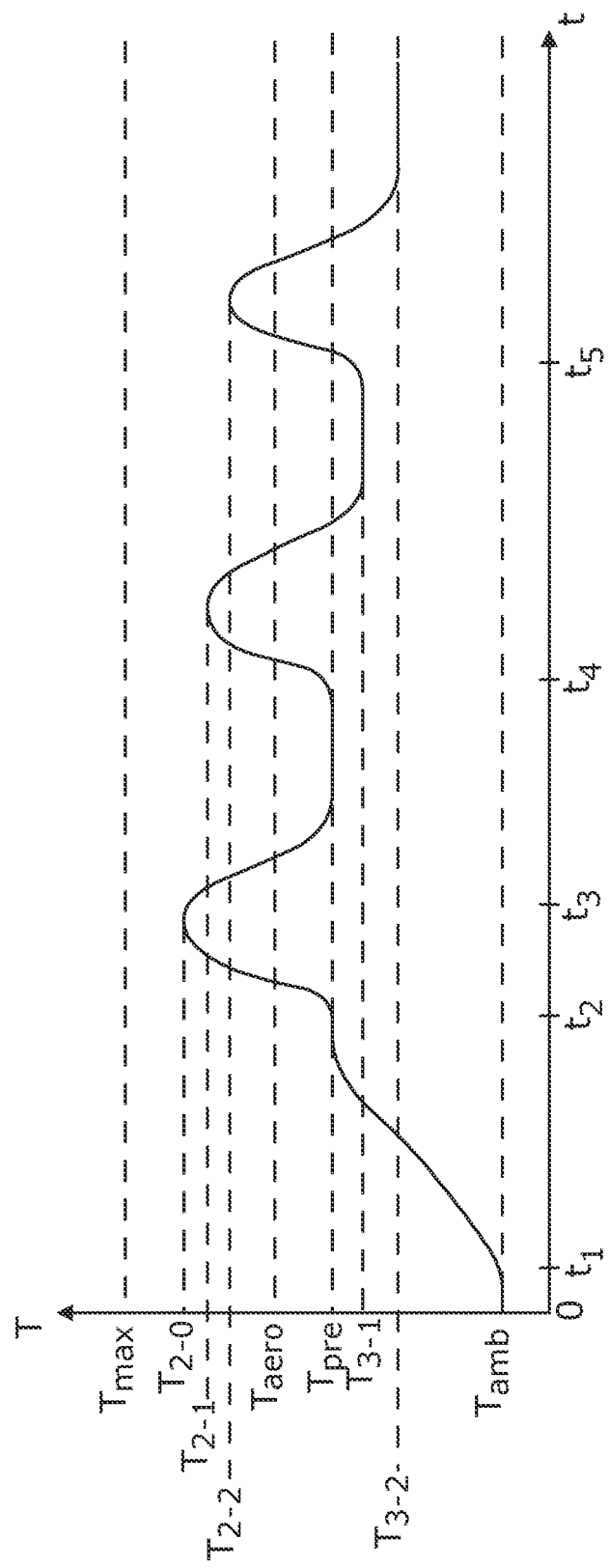

FIG. 5C illustrates a combination of the features illustrated in FIGS. 5A and 5B—in essence, both the aerosolisation temperature and the preconditioning temperatures are progressively reduced between successive device activations, but notably the effect of these adjustments can be that the effective area under the profile curve (the skilled reader will be well aware of the AUC or "area under curve" metric used in pharmacokinetics and drug delivery) during any of the three activations illustrated is broadly the same.

Figure 5D:
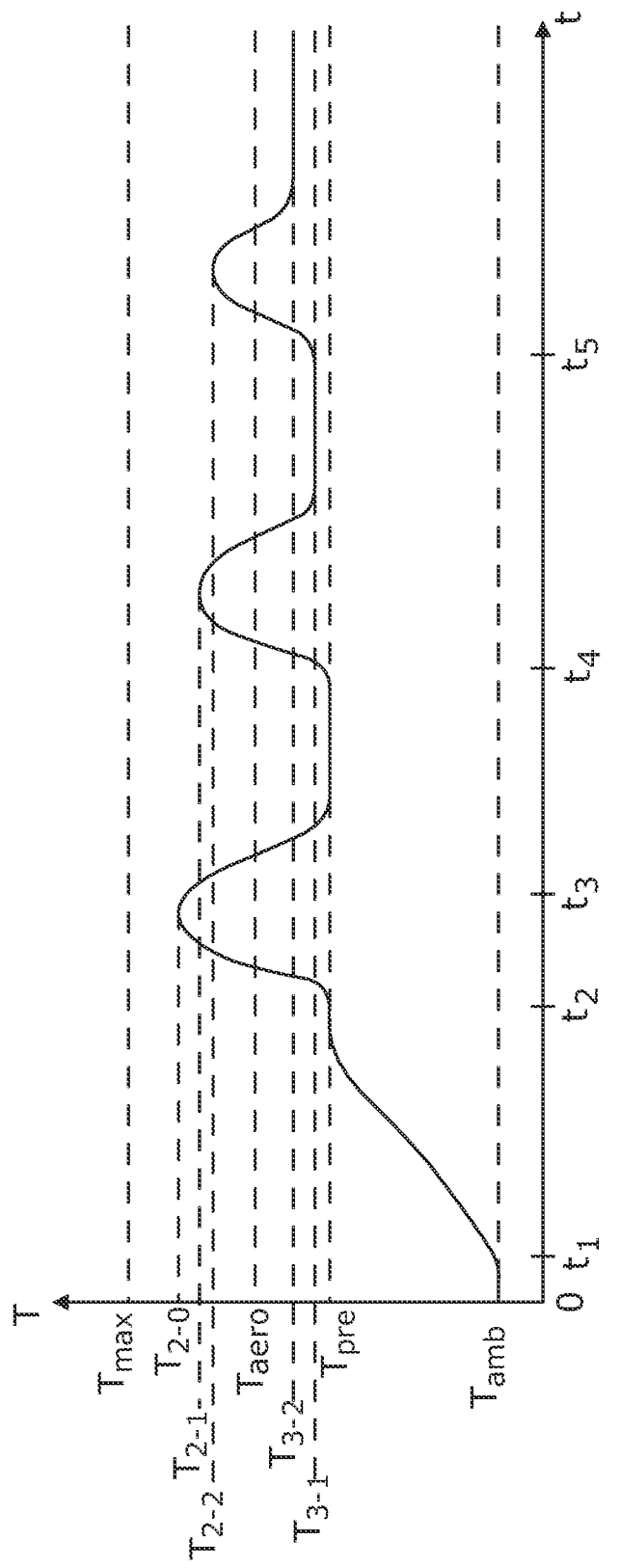

FIG. 5D illustrates a different combination of the features illustrated in FIGS. 5A and 5B—in this Figure, the aerosolisation temperatures are shown as progressively reducing between successive activations whereas the preconditioning temperature is shown as progressively increasing between successive device activations, so in this case the effect of these adjustments is that the effective area under the profile curve is significantly reduced between the first, second and third activations.

Figure 5E:
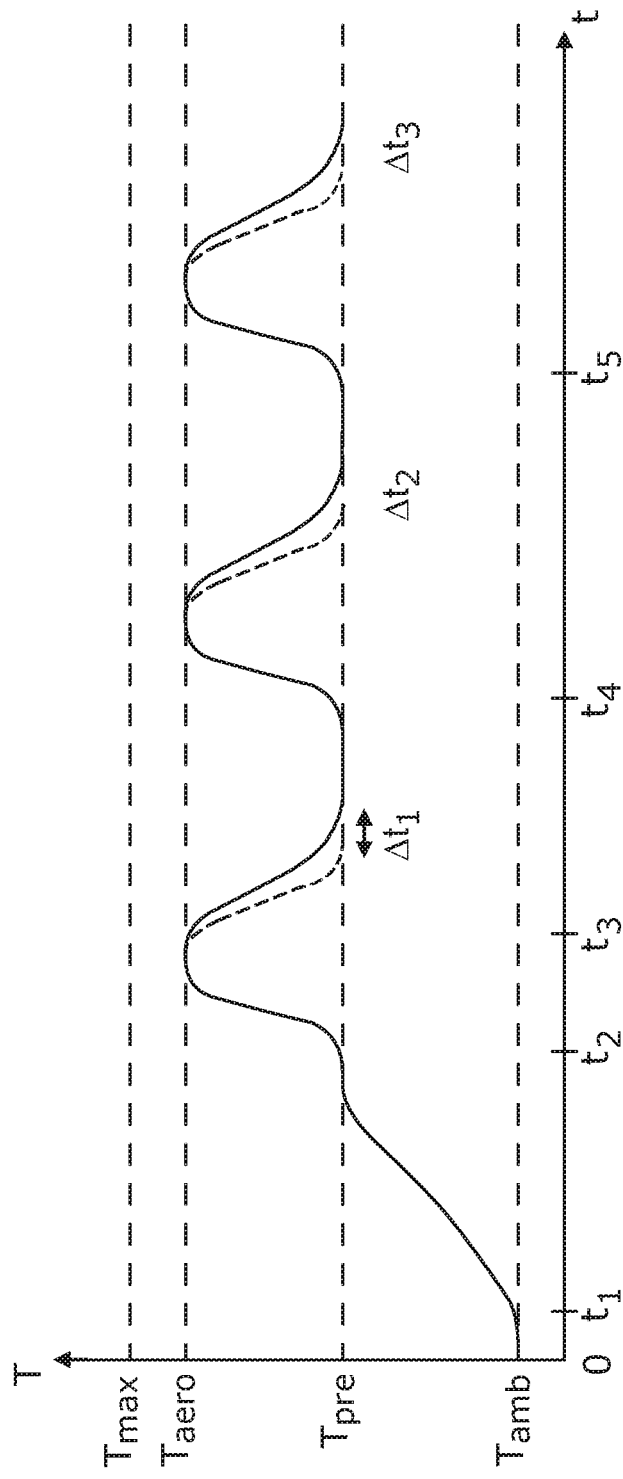

FIG. 5E illustrates a particular aspect of the present invention wherein the rate of cooling as between successive activations can be adjusted. As can be seen in the figure, each activation $t_2$ $t_4$ $t_5$ includes a tail-end cooling phase, where the heater cools from the aerosolisation temperature to the preconditioning temperature. The dashed lines in this Figure indicate the theoretical maximum (unassisted) cooling rates achievable under pure Newtonian cooling. As can be seen however, the solid line cooling profiles for each activation result in the cooling phases taking progressively longer than the theoretical minimum cooling times, by amount $\Delta t_1$, $\Delta t_2$, $\Delta t_3$, as may be desired. This feature may be of benefit in certain circumstances, and may of course be combined with other features mentioned above in relation to FIGS. 5A-5D. Modulating the cooling rate in this manner can prevent the issue of thermal shock from arising.

Importantly, all the heating profiles in FIG. 5 and FIGS. 5A-5E all allow for modulation of the dose of a medicament such as nicotine in each different, separate inhalation while the device is being used in any operative period. In some embodiments, it may be possible to achieve an approximately identical dose of nicotine in every inhalation, even as the amount of aerosolisable composition decreases, or in other embodiments it may be possible to progressively modulate the nicotine concentration between the first and successive subsequent device activations. This latter arrangement is particularly preferable, because it is widely believed that the concentration of nicotine varies with each inhalation from a conventional cigarette, and therefore the device of the present invention can be programmed to very accurately reflect the nicotine delivery characteristics of a conventional cigarette, which can be invaluable when it comes to weening smokers away from cigarettes, which are of course significantly more harmful.

Furthermore, it may be possible to control the power to the heater such that only a relatively low dose of nicotine is delivered to the user initially, with relatively much greater doses being delivered in subsequent successive device activations—this can make the delivery of nicotine more tolerable because it reduces the concentration of nicotine for initial inhalations, but as the throat becomes accustomed to the inhalation of nicotine-bearing vapour, nicotine concentrations can be increased. It is worth noting that high levels of nicotine in a single inhalation can irritate the airways causing mild, or in some cases severe, coughing. In FIGS. 5, 5A-5E, although only three activations are illustrated, it is to be understood that a typical number of activations may be between 5-10 (for cigarette smokers, possibly more for cigar and pipe smokers) during a single operative use of the device. As mentioned previously, if a further activation of the device is not forthcoming within a predetermined amount of time after the last activation, the device will shut itself down. In some embodiments, the device may be somewhat self-aware in that it is aware of the cartridge currently in place and the typical amount of aerosolisable composition provided therein, and maintains a count of the number of previous activations which have occurred since the last new cartridge was inserted so that some determination or estimation can be made by the device as to the number of permissible activations remaining for that cartridge before it is effectively spent. In such cases, and if the device determines that the cartridge is spent, then it may also shut itself down.

Figure 6:
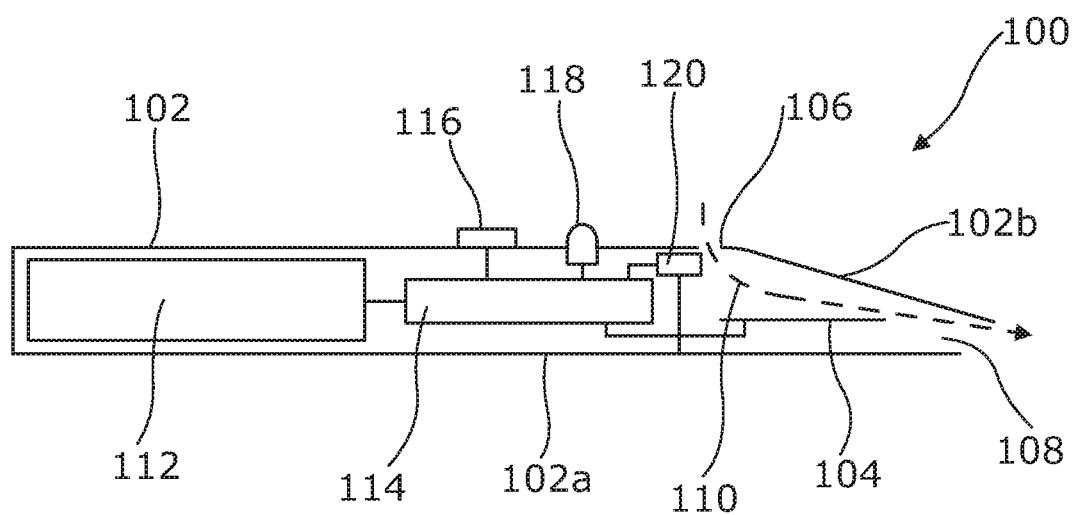

FIG. 6 shows a schematic illustration of an embodiment of an inhalation device in a simplified manner. The illustration has not been drawn to scale and omits features which are not important to the understanding of the embodiment. The inhalation device 100 comprises a housing 102 having a main body part 102a and a mouthpiece 102b. The mouthpiece 102b is removably attachable to the main body part 102a. A heater 104 is arranged within the mouthpiece 102b. The heater 104 comprises a flat substrate on which a resistive heater element (not shown) is supported, for example, by screen printing the resistive heater element on the substrate.

An amount of aerosolisable composition (not shown) is deposited on and supported by the heater 104, and both will be generally supported the underlying substrate, which in most cases will be essentially planar and usually small (10 mm×20 mm×2 mm) and rectangular in shape. The aerosolisable composition is ideally disposed over the resistive element part of the heater so that the heater transfers the majority of its heat directly into the composition. Ideally, the heater 104 comes preloaded with a known amount of the aerosolisable composition to be aerosolised. The mouthpiece 102b and heater 104 may form a heater-mouthpiece subassembly which is provided as a replaceable consumable for attachment to the main body part 102a which can be replaced once the amount of aerosolisable composition on the heater 104 has been expended.

The inhalation device 100 comprises an air inlet 106 and an air outlet 108. An airflow pathway 110 passes from the air inlet 106, through the device in the vicinity of the heater 104 and exits via air outlet 108. In use, aerosolised composition is entrained in the airflow passing along airflow pathway 110 and is inhaled by a user via air outlet 108.

The inhalation device 100 is electrically heated and comprises a power source 112, for example, a rechargeable lithium ion battery, located within the main body part 102a for providing electrical power to the heater 104. The power source 112 is connected to a controller 114, for example, a microcontroller, which in turn is connected to the heater 104 to control the power delivered to the heater 104.

A switch 116 is arranged on the external surface of the main body part 102 and is connected to the controller 114. The switch 116 constitutes a sensor which can be activated by a user to send a signal to the controller 114 to heat the heater 104 to a first temperature or preconditioning temperature. The inhalation device 100 further comprises an LED 118 connected to the controller 114 which acts as an indicator and may be illuminated to inform a user that the heater is at the preconditioning temperature. In addition, a sensor 120, such as a flow sensor or pressure transducer, is connected to the controller 114 and sends a signal to the controller 114 when airflow through airflow pathway 110 due to a user's inhalation is detected. Responsive to the signal from sensor 120, the controller 114 controls the power delivered to the heater 104 to heat the heater 104 to a second temperature or aerosolisation temperature.

Figure 7:
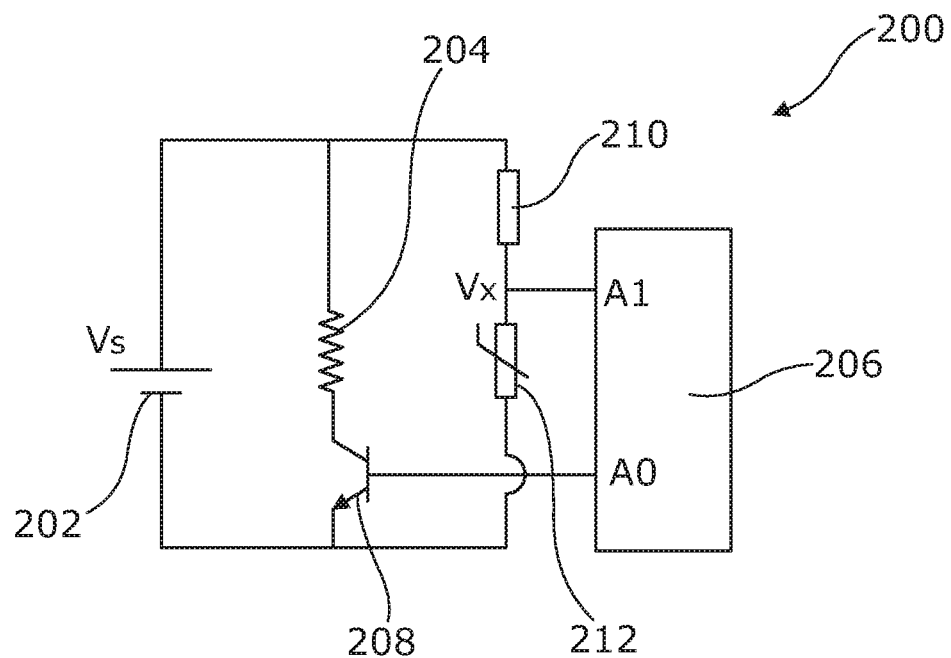
FIG. 7 is a schematic circuit diagram of a controller of an inhalation device according to an embodiment of the present invention.
Figure 8:
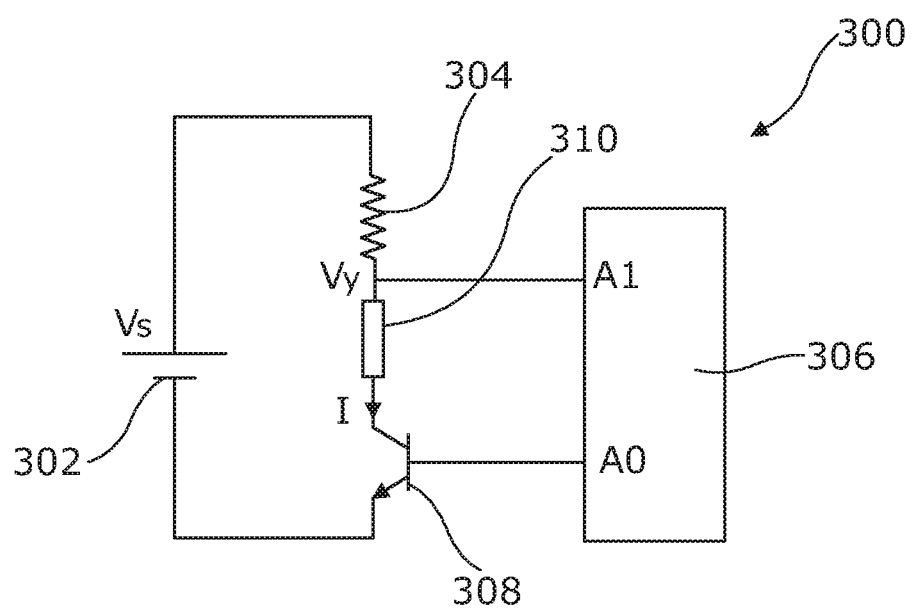
FIG. 8 is a schematic circuit diagram of a controller of an inhalation device according to another embodiment of the present invention.

FIGS. 7, 8 show possible simple electric/electronic circuits which illustrate basic possible arrangements of components, and how they might function together. These arrangement are provided only for example and are not to be considered as limiting the invention. Alternate circuits and arrangements may of course be devised which could nevertheless achieve the same overall functionality of the present invention, and such would therefore be considered to fall within the scope hereof. Furthermore, although not repeated for brevity, it should be mentioned that the controller components 114, 206, 306 are capable, and indeed required in some aspects of the present invention, to make an initial determination of some value representative of the ambient temperature, and then (in some embodiments) to store this value, and to subsequent control power to the heater in a manner which is at least partially dependent on the value so determined.

FIG. 7 shows circuitry 200 for controlling the heater of an inhalation device in order to provide the heating profiles described above in accordance with an embodiment of the invention. A power source 202 provides a supply voltage $V_S$ to the circuit. A resistive heater element 204 of the heater is controlled by an analogue output AO of a microcontroller 206 via a transistor 208 which acts as a switch. A resistor 210 of known resistance $R_1$ is arranged in series with a thermistor 212. The series combination of the resistor 210 and thermistor 212 is arranged in parallel with the resistive heater element 204 and transistor 208 combination and in parallel with the power source 202. The resistor 210 and thermistor 212 therefore form a voltage divider of the supply voltage $V_S$. A point in the circuit intermediate the resistor 210 and thermistor 212 is connected to an analogue input AI of the controller 206 to read the voltage $V_X$ at that point, i.e. the voltage across the thermistor 212.

In the inhalation device, the thermistor 212 is arranged adjacent or near to the resistive heater element 204 such that, in use, it is in thermal contact with the resistive heater element 204 to determine its temperature. Responsive to an initial activation by the user, the microcontroller 206 starts to deliver power to the resistive heater element 204 via transistor 208 in order to increase the temperature of the resistive heater element 204 towards the preconditioning temperature. The resistance $R_{TH}$ of the thermistor 212 varies with temperature, which in turn causes the voltage $V_X$ to vary in accordance with the following equation:

$$V_X = V_S \cdot \frac{R_{TH}}{R_{TH} + R_1} \quad (1)$$

A look-up table of voltages $V_X$ and corresponding temperatures may be stored within a memory of the microcontroller 206 and used to determine the temperature of the resistive heater element 204 when a certain voltage $V_X$ is read by the microcontroller 206. Alternatively, the resistance $R_{TH}$ of the thermistor 212 can be determined by rearranging equation (1) and using the known values of $V_X$ and $R_1$. The temperature of the resistive heater element 204 can then be determined either from a look-up table of resistances and corresponding temperatures or by interpolating the temperature based on the determined resistance $R_{TH}$ and information stored in memory of the microcontroller 206 relating to the variation of $R_{TH}$ with temperature and a known resistance and a temperature, for example, the value of $R_{TH}$ at 25° C.

Based on the determined temperature of the resistive heater element 204, the power delivered to the resistive heater element 204 can be controlled to drive its temperature towards the preconditioning temperature. The control of the power is based on a PID control loop which is implemented within a computer program or other software or firmware stored within the microcontroller 206. If the microcontroller 206 has a digital-to-analogue converter (DAC), the power delivered to the resistive heater element 204 can be controlled by simply controlling the voltage delivered by the analogue output AO of the microcontroller 206, which in turn controls the biasing voltage of the transistor 208 and therefore the current that passes through the resistive heater element 204. Alternatively, the transistor can be controlled by a digital output (not shown) of the microcontroller 206. In this arrangement, the microcontroller 206 pulse width modulates (PWM) the digital output such that the power delivered to the resistive heater element 204 is determined by the duty cycle of the modulated voltage signal, i.e. the percentage of time the digital output is switched on.

Once the resistive heater element 204 has reached the predetermined temperature, the controller 206 awaits a further activation signal that a user wishes to generate an aerosolised composition for inhalation. In response to this further activation signal the microcontroller 206 increases the power delivered to the resistive heater element 204 by a predetermined amount so as to increase the temperature of the heater to an aerosolisation temperature. This can be done by increasing the analogue voltage at the analogue output of the microcontroller 206 by a certain amount or by increasing the duty cycle of the pulse width modulated signal by a certain percentage. Once the inhalation is finished, the microcontroller 206 controls the power delivered to the resistive heater element 206 such that it returns to the preconditioning temperature or, if the maximum number of inhalations has been reached to deliver a certain dose, to cease delivering power to the resistive heater element 204.

FIG. 8 shows circuitry 300 for controlling the heater of an inhalation device in order to provide the heating profiles described above in accordance with another embodiment of the invention. A power source 302 provides a supply voltage $V_S$ to the circuit. A resistive heater element 304 of the heater is controlled by an analogue output AO of a microcontroller 306 via a transistor 308 which acts as a switch. A resistor 310 of known resistance $R_2$ is arranged in series with the resistive heater element 304 at a point intermediate between the resistive heater element 304 and the transistor 308. A point in the circuit intermediate the resistive heater element 304 and the resistor 310 is connected to an analogue input AI of the controller 306 to read the voltage $V_Y$ at that point.

The control circuitry 300 is configured to determine the resistance $R_H$ of the resistive heater element 304. The resistance $R_H$ is dependent on or proportional to temperature; as the temperature of the resistive heater element 304 increases, the resistance $R_H$ also increases. Therefore, the resistance $R_H$ provides an indicator of the temperature of the resistive heater element 304. An advantage of this circuit compared to that of FIG. 7 is that it does not need a thermistor. The temperature or an indication of the temperature is determined based on the resistance $R_H$ of the resistive heater element 304. This reduces the part count of the device and complexity of the circuit and control program.

The resistance $R_H$ can be determined from Ohm's Law according to the equation:

$$R_H = \frac{V_H}{I} \quad (2)$$

where $V_H$ is the voltage across the resistive heater element 304 and I is the current flowing through the resistive heater element 304.

The voltage $V_H$ across the resistive heater element 304 is equal to $V_S - V_Y$, i.e. the supply voltage $V_S$, which is known, minus the voltage $V_Y$ measured at the point intermediate the resistive heater element 304 and the resistor 310, which is read by the microcontroller 306.

The current I flowing through the resistive heater element 304 is equal to the current flowing through the resistor 310 because they are in series and therefore the current I can be determined from Ohm's Law according to the equation:

$$I = \frac{V_Y}{R_2} \quad (3)$$

The resistance $R_2$ of the resistor 310 is also known. Therefore, substituting the equations for $V_H$ and I into equation (2) gives the following equation for determining $R_H$:

$$R_H = \frac{(V_S - V_Y)}{V_Y} \cdot R_2 \quad (4)$$

Once $R_H$ is known, the temperature $T_H$ of the resistive heater element 304 corresponding to the measured resistance $R_H$ can be determined using a linear approximation based on the temperature coefficient of resistance a and given a reference resistance $R_{REF}$ of the resistive heater element 304 at a reference temperature $T_{REF}$ in accordance with the following equation:

$$T_H = \frac{R_H}{\alpha R_{REF}} - \frac{1}{\alpha} + T_{REF} \quad (5)$$

The reference resistance $R_{REF}$ could be determined using ambient temperature as the reference temperature $T_{REF}$ when the device is initially activated in accordance with the same method for determining $R_H$ described above.

Based on the determined temperature $T_H$ of the resistive heater element 304, the power delivered to the resistive heater element 304 can be controlled to drive its temperature towards the preconditioning temperature. The control of the power is based on a PID control loop which is implemented within a computer program or other software or firmware stored within the microcontroller 306. If the microcontroller 306 has a digital-to-analogue converter (DAC), the power delivered to the resistive heater element 304 can be controlled by simply controlling the voltage delivered by the analogue output AO of the microcontroller 306, which in turn controls the biasing voltage of the transistor 308 and therefore the current that passes through the resistive heater element 304. Alternatively, the transistor can be controlled by a digital output (not shown) of the microcontroller 306. In this arrangement, the microcontroller 306 pulse width modulates (PWM) the digital output such that the power delivered to the resistive heater element 304 is determined by the duty cycle of the modulated voltage signal, i.e. the percentage of time the digital output is switched on.

Once the resistive heater element 304 has reached the predetermined temperature, the controller 306 awaits a further activation signal that a user wishes to generate an aerosolised composition for inhalation. In response to this further activation signal the microcontroller 306 increases the power delivered to the resistive heater element 304 by a predetermined amount so as to increase the temperature of the heater to an aerosolisation temperature. This can be done by increasing the analogue voltage at the analogue output of the microcontroller 306 by a certain amount or by increasing the duty cycle of the pulse width modulated signal by a certain percentage. Once the inhalation is finished, the microcontroller 306 controls the power delivered to the resistive heater element 306 such that it returns to the preconditioning temperature or, if the maximum number of inhalations has been reached to deliver a certain dose, to cease delivering power to the resistive heater element 304.

In view of the foregoing description it will be evident to a person skilled in the art that various modifications may be made within the scope of the invention. For example, Instead of a resistive heater element screen printed on a substrate, other types of heater may be used such as heaters comprising resistive metal alloys or ceramics.

Rather than use a single resistor of a known value to determine the resistance of the resistive heater element, three resistors of known value and the resistive heater element arranged in a Wheatstone bridge configuration may be used. This may provide for improved accuracy in determining and controlling the temperature of the resistive heater element up to the preconditioning temperature.

Furthermore, in the determination of the temperature of the resistive heater element, rather than rely on a known value of the supply voltage, the supply voltage may be read by a further analogue input of the microcontroller to accurately determine the supply voltage. This may assist in reducing inaccuracies due to variations in the power supplied by the power source, for example, when it starts to lose its charge.

The scope of the present disclosure includes any novel feature or combination of features disclosed therein either explicitly or implicitly or any generalisation thereof irrespective of whether or not it relates to the claimed invention or mitigate against any or all of the problems addressed by the present invention. The applicant hereby gives notice that new claims may be formulated to such features during prosecution of this application or of any such further application derived therefrom. In particular, with reference to the appended claims, features from dependent claims may be combined with those of the independent claims and features from respective independent claims may be combined in any appropriate manner and not merely in specific combinations enumerated in the claims.

The invention claimed is:

1. A method of controlling the generation of an aerosolised composition in an inhalation device having:
    a power source,
    means for determining an ambient temperature,
    a controller, and
    an electrically resistive heater connected to said controller and arranged to heat an aerosolisable composition,
    the method comprising the steps of:
    upon the device initially becoming operative, determining a value representative of the ambient temperature and controlling the power supplied to the heater in dependence on said value such that the heater is heated at an initial heating rate from said ambient temperature to an initial preconditioning temperature being below an aerosolisation temperature of the aerosolisable composition, and thereafter maintaining the temperature of the heater at said initial preconditioning temperature, being the prevailing temperature until a first activation of the device;
    and then, while the device is operative, subsequently activating said device a plurality of times, each such activation comprising:
    (A) controlling the power supplied to the heater such that the temperature of the heater is increased at a respective activation heating rate from the prevailing heater temperature to a respective secondary temperature and thereafter maintaining the heater at said respective secondary temperature during said activation, said respective secondary temperature being greater than or equal to the aerosolisation temperature,
    and then, after the completion of each such activation,
    (B) controlling the power supplied to the heater such that the temperature of the heater decreases at a respective post-activation cooling rate from said respective secondary temperature to a respective further preconditioning temperature being below the aerosolisation temperature but above the ambient temperature, and thereafter maintaining the temperature of said heater at said respective further preconditioning temperature, being the prevailing temperature until the next activation, wherein either one or both of the following applies:

the power to the heater is controlled such that there is progressive change in the secondary temperature of any one activation as compared to the secondary temperature or temperature(s) of any one or more previous activations, and the power to the heater is controlled such that there is a progressive change in the preconditioning temperature prevailing at the commencement of any one activation as compared to the preconditioning temperature or temperatures prevailing at the commencement of any one or more previous activations.

2. The method according to claim 1, wherein the maintaining of the heater at any one or more of the preconditioning temperatures and the secondary temperatures is achieved by dynamically measuring the heater temperature or a value representative thereof and comparing said dynamically measured heater temperature or value with a value representative of a desired temperature to be achieved, and controlling the power to the heater accordingly.

3. The method according to claim 1, wherein a feedback mechanism is employed to control the power delivered to the heater dynamically.

4. The method according to claim 1, wherein the preconditioning temperatures are within any one of the following ranges: 25° C. to 90° C., 30° C. to 70° C., 35° C. to 50° C.

5. The method according to claim 1, wherein the secondary temperatures are within any one of the following ranges: 120° C. to 190° C., 130° C. to 170° C., 140° C. to 160° C.

6. The method according to claim 1, wherein:

the duration of each and every activation is in the range 0.5-6 s, any one activation being initiated by either or both of: a simple switch, and automatically by one of an air pressure sensor and an air flow sensor, and wherein deactivation is caused to occur by one of: release or a change in state of a simple switch, automatically when an air pressure sensor or an air flow sensor ceases to indicate a pressure drop or an air flow, and after a predetermined period of time.

7. The method according to claim 1, wherein a value representing the ambient temperature is initially determined and stored in one of: a volatile memory, a non-volatile memory, provided within the device.

8. The method according to claim 1, including the further steps of using one or more look-up tables to correlate measured heater resistance values with temperature, and comparing a temperature value so determined with a desired heater temperature to be obtained, or at which the heater is to be maintained.

9. The method according to claim 1, wherein the heater is heated such that it returns to one of the preconditioning temperatures after being heated to one of the secondary temperatures according to one of the following: less than 20 times, between 8 and 15 times, between 5 and 10 times.

10. The method according to claim 1, wherein the progressive change to one or both of the secondary temperatures and the preconditioning temperatures is one of: a progressive increase, a progressive decrease.

11. The method according to claim 1, wherein the power to heater is controlled such that each post-activation cooling rate is modified as compared to the natural rate of cooling which would occur if no power whatsoever were delivered to the heater during such a time.

12. The method according to claim 11, wherein the power to the heater is controlled such that the post-activation cooling rate occurring immediately after one activation progressively changes as compared with the post-activation cooling rate or rates occurring immediately after one or more previous activations.

13. The method according to claim 1, wherein one or more of the following applies:

The secondary temperatures remain essentially constant between any two or more successive device activations, whereas the preconditioning temperatures change progressively between successive activations, and The preconditioning temperatures remain essentially constant between any two or more successive activations, whereas the secondary temperatures change progressively between any two or more successive activations.

14. The method according to claim 1, wherein the power to the heater is controlled such that the initial heating rate is slower than the activation heating rates.

15. An inhalation device comprising a power source, means for determining an ambient temperature, a controller, and an electrically resistive heater connected to said controller, the inhalation device configured to carry out a method comprising the steps of:

upon the device initially becoming operative, determining a value representative of the ambient temperature and controlling the power supplied to the heater in dependence on said value such that the heater is heated at an initial heating rate from said ambient temperature to an initial preconditioning temperature being below an aerosolisation temperature of the aerosolisable composition, and thereafter maintaining the temperature of the heater at said initial preconditioning temperature, being the prevailing temperature until a first activation of the device;

and then, while the device is operative, subsequently activating said device a plurality of times, each such activation comprising:

(A) controlling the power supplied to the heater such that the temperature of the heater is increased at a respective activation heating rate from the prevailing heater temperature to a respective secondary temperature and thereafter maintaining the heater at said respective secondary temperature during said activation, said respective secondary temperature being greater than or equal to the aerosolisation temperature, and then, after the completion of each such activation, (B) controlling the power supplied to the heater such that the temperature of the heater decreases at a respective post-activation cooling rate from said respective secondary temperature to a respective further preconditioning temperature being below the aerosolisation temperature but above the ambient temperature, and thereafter maintaining the temperature of said heater at said respective further preconditioning temperature, being the prevailing temperature until the next activation, wherein either one or both of the following applies:

the power to the heater is controlled such that there is progressive change in the secondary temperature of any one activation as compared to the secondary temperature or temperature(s) of any one or more previous activations, and the power to the heater is controlled such that there is a progressive change in the preconditioning temperature prevailing at the commencement of any one activation as compared to the preconditioning temperature or temperatures prevailing at the commencement of any one or more previous activations.

16. The inhalation device according to claim 15, wherein the inhalation device is a cartridge-type device wherein the heater is provided on a planar substrate on which is further deposited, in a relevant area thereon where the heater will have a heating effect, an amount of an aerosolisable composition such that the substrate supports both the heater and the aerosolisable composition, and wherein together, the substrate, heater and aerosolisable composition are provided together in the form of a cartridge which can be removed from the device when spent, and thereafter replaced with a fresh cartridge.

17. The inhalation device according to claim 16, wherein the substrate is of a material selected from one or more of: a ceramic, a plastics and glass.

18. The inhalation device according to claim 15, the inhalation device further comprising one or both of:

a first operative device, in communication with the controller, which, when operated or caused to operate by a user causes the inhalation device to enter an operative state, and activation means, whereby the inhalation device is or is caused to be activated and in which state an aerosol is caused to be created from the aerosolisable composition.

19. A computer program for operating an inhalation device, the inhalation device comprising a power source, means for determining an ambient temperature, a controller executed by the computer program, and an electrically resistive heater connected to said controller, the computer program adapted to cause power to the heater to be controlled in a method comprising the steps of:

upon the device initially becoming operative, determining a value representative of the ambient temperature and controlling the power supplied to the heater in dependence on said value such that the heater is heated at an initial heating rate from said ambient temperature to an initial preconditioning temperature being below an aerosolisation temperature of the aerosolisable composition, and thereafter maintaining the temperature of the heater at said initial preconditioning temperature, being the prevailing temperature until a first activation of the device;

and then, while the device is operative, subsequently activating said device a plurality of times, each such activation comprising:

(A) controlling the power supplied to the heater such that the temperature of the heater is increased at a respective activation heating rate from the prevailing heater temperature to a respective secondary temperature and thereafter maintaining the heater at said respective secondary temperature during said activation, said respective secondary temperature being greater than or equal to the aerosolisation temperature, and then, after the completion of each such activation, (B) controlling the power supplied to the heater such that the temperature of the heater decreases at a respective post-activation cooling rate from said respective secondary temperature to a respective further preconditioning temperature being below the aerosolisation temperature but above the ambient temperature, and thereafter maintaining the temperature of said heater at said respective further preconditioning temperature, being the prevailing temperature until the next activation, wherein either one or both of the following applies:

the power to the heater is controlled such that there is progressive change in the secondary temperature of any one activation as compared to the secondary temperature or temperature(s) of any one or more previous activations, and the power to the heater is controlled such that there is a progressive change in the preconditioning temperature prevailing at the commencement of any one activation as compared to the preconditioning temperature or temperatures prevailing at the commencement of any one or more previous activations.

20. A computer readable storage medium having stored thereon a computer program for operating an inhalation device, the inhalation device comprising a power source, means for determining an ambient temperature, a controller executed by the computer program, and an electrically resistive heater connected to said controller, the computer program adapted to cause power to the heater to be controlled in a method comprising the steps of:

upon the device initially becoming operative, determining a value representative of the ambient temperature and controlling the power supplied to the heater in dependence on said value such that the heater is heated at an initial heating rate from said ambient temperature to an initial preconditioning temperature being below an aerosolisation temperature of the aerosolisable composition, and thereafter maintaining the temperature of the heater at said initial preconditioning temperature, being the prevailing temperature until a first activation of the device;

and then, while the device is operative, subsequently activating said device a plurality of times, each such activation comprising:

(A) controlling the power supplied to the heater such that the temperature of the heater is increased at a respective activation heating rate from the prevailing heater temperature to a respective secondary temperature and thereafter maintaining the heater at said respective secondary temperature during said activation, said respective secondary temperature being greater than or equal to the aerosolisation temperature, and then, after the completion of each such activation, (B) controlling the power supplied to the heater such that the temperature of the heater decreases at a respective post-activation cooling rate from said respective secondary temperature to a respective further preconditioning temperature being below the aerosolisation temperature but above the ambient temperature, and thereafter maintaining the temperature of said heater at said respective further preconditioning temperature, being the prevailing temperature until the next activation, wherein either one or both of the following applies:

the power to the heater is controlled such that there is progressive change in the secondary temperature of any one activation as compared to the secondary temperature or temperature(s) of any one or more previous activations, and the power to the heater is controlled such that there is a progressive change in the preconditioning temperature prevailing at the commencement of any one activation as compared to the preconditioning temperature or temperatures prevailing at the commencement of any one or more previous activations.

* * * * *